United States Patent
Schaus et al.

(10) Patent No.: US 9,175,001 B2
(45) Date of Patent: Nov. 3, 2015

(54) [1,3] DIOXOLO [4,5-G] [1,2,4] TRIAZOLO [1,5-A] QUINOLINE DERIVATIVES AS INHIBITORS OF THE LATE SV40 FACTOR (LSF) FOR USE IN TREATING CANCER

(71) Applicant: TRUSTEES OF BOSTON UNIVERSITY, Boston, MA (US)

(72) Inventors: Scott E. Schaus, Boston, MA (US); Ulla Hansen, Bedford, MA (US); Joshua A. Bishop, Southborough, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 14/349,230

(22) PCT Filed: Oct. 2, 2012

(86) PCT No.: PCT/US2012/058433
§ 371 (c)(1),
(2) Date: Apr. 2, 2014

(87) PCT Pub. No.: WO2013/052465
PCT Pub. Date: Apr. 11, 2013

(65) Prior Publication Data
US 2014/0249312 A1    Sep. 4, 2014

Related U.S. Application Data

(60) Provisional application No. 61/585,272, filed on Jan. 11, 2012, provisional application No. 61/542,245, filed on Oct. 2, 2011.

(51) Int. Cl.
*C07D 491/00* (2006.01)
*C07D 491/056* (2006.01)
*C07D 491/147* (2006.01)

(52) U.S. Cl.
CPC ........ *C07D 491/056* (2013.01); *C07D 491/147* (2013.01)

(58) Field of Classification Search
None
See application file for complete search history.

(56) References Cited

U.S. PATENT DOCUMENTS 5,968,952 A    10/1999    Venet et al.

FOREIGN PATENT DOCUMENTS

| WO | 2012050985 | | 4/2012 |
| WO | WO2012050985 A1 | * | 4/2012 |
| WO | 2012027392 | | 5/2012 |

OTHER PUBLICATIONS

CAPLUS 2008:1549605.*
CAPLUS 2008 1549605.*
Li-Ping Guan et al: "Synthesis and Anticonvulsant Activity of 5-Phenyl-[1,2,4]-triazolo[4,3-a]quinolines", Archiv Der Pharmazie, 341(12):774-779 (Dec. 1, 2008).
Pragya Singh et al: "Design and Synthesis of C-Ring Lactone- and Lactam-Based Podophyllotoxin Analogues as Anticancer Agents", Chemical & Pharmaceutical Bulletin, 58(2):242-246 (Feb. 1, 2010).
Yu-Hsun Chang et al: "Design and Synthesis of 2-(3-Benzo[ b ]thienyl)-6,7-methylenedioxyquinolin-4-one Analogues as Potent Antitumor Agents that Inhibit Tubulin Assembly", Journal of Medicinal Chemistry, 52 (15):4883-4891 (Aug. 13, 2009).

* cited by examiner

*Primary Examiner* — Heidi Reese
(74) *Attorney, Agent, or Firm* — Nixon Peabody LLP

(57) ABSTRACT

The present invention relates generally to [1,3]dioxolo[4,5-g]quinoline-6(5H)thione and [1,3]dioxolo[4,5-g][1,2,4]triazolo[1,5-a]quinoline derivatives and/or compositions for use in inhibiting, preventing and/or treating cancer, e.g. hepatocellular carcinoma (HCC). In some embodiments, the invention relates to the use of small-molecule compounds to inhibit, prevent and/or treat expression of the transcription factor Late SV40 Factor (LSF) for treatment of HCC or other cancer types.

10 Claims, 8 Drawing Sheets

Thio Compounds

I
S-Enantiomer

II
R-Enantiomer

III
Not Chiral

Tautomeric Forms

III-1   III-2

Thio Compounds

XI
S-Enantiomer

XII
R-Enantiomer

XIII
Not Chiral

Triazole Compounds

IV

S-Enantiomer

V

R-Enantiomer

VI

Not Chiral

Triazole Compounds

XIV
S-Enantiomer

XV
R-Enantiomer

XVI
Not Chiral

Racemic Mixture of Compounds I and II

Racemic Mixture of Compounds IV & V

Compound VI

Compound VI – also known as LB-242

[1,3] DIOXOLO [4,5-G] [1,2,4] TRIAZOLO [1,5-A] QUINOLINE DERIVATIVES AS INHIBITORS OF THE LATE SV40 FACTOR (LSF) FOR USE IN TREATING CANCER

CROSS REFERENCE TO RELATED APPLICATIONS

This application is a 35 U.S.C. §371 National Phase Entry Application of International Application No. PCT/US2012/058433 filed Oct. 2, 2012, which designates the U.S., and which claims benefit under one or more of 35 U.S.C. §119(e) of U.S. Provisional Application No.: 61/542,245, filed on Oct. 2, 2011 and U.S. Provisional Application No.: 61/585,272, filed on Jan. 11, 2012,the contents of each of which are incorporated herein by reference in their entireties.

STATEMENT REGARDING FEDERALLY SPONSORED RESEARCH OR DEVELOPMENT

This invention was made with Government Support under Contract No. GM067041 awarded by the National Institutes of Health. The Government has certain rights in the invention.

The section headings used herein are for organizational purposes only and should not be construed as limiting the subject matter described in any way.

BRIEF DESCRIPTION OF DRAWINGS

The skilled artisan will understand that the drawings, described below, are for illustration purposes only. The drawings are not intended to limit the scope of the present teaching in any way.

In the drawings, the sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn may not be intended to convey any information regarding the actual shape of the particular elements, and may have been selected solely for ease of recognition in the drawings.

Figure 1:
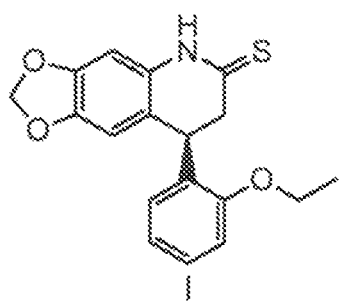
FIG. 1 is an illustration of: (i) the S-enantiomer of a thio-containing therapeutic compound of structural formula I; (ii) the R-enantiomer of a thio-containing therapeutic compound of structural formula II, (iii) a non-chiral thio-containing therapeutic compound of structural formula III; and the two tautomeric forms (i.e. III-1 and III-2) of the compound of structural formula III.
Figure 1:
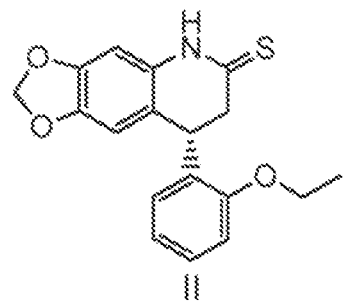
Figure 1:
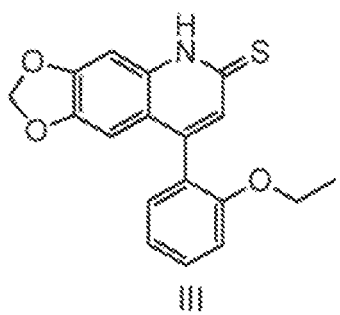
Figure 1:
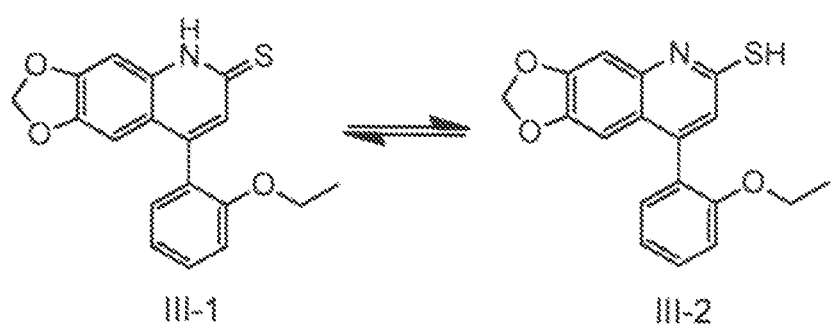
Figure 2:
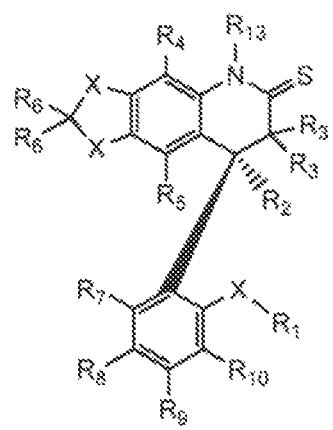
FIG. 2 is an illustration of: (i) a generic structure (i.e. XI) for the S-enantiomer of a thio-containing therapeutic compound of structural formula I wherein the variables $R_1$, $R_2$, $R_3$, $R_4$, $R_5$, $R_6$, $R_7$, $R_8$, $R_9$, $R_{10}$ and $R_{13}$ are defined herein; (ii) a generic structure (i.e. XII) for the R-enantiomer of a thio-containing therapeutic compound of structural formula II wherein the variables $R_1$, $R_2$, $R_3$, $R_4$, $R_5$, $R_6$, $R_7$, $R_8$, $R_9$, $R_{10}$ and $R_{13}$ are defined herein, (iii) a generic structure (i.e. XIII) for a non-chiral thio-containing therapeutic compound of structural formula III wherein the variables $R_1$, $R_4$, $R_5$, $R_6$, $R_7$, $R_8$, $R_9$, $R_{10}$, $R_{11}$ and $R_{13}$ are defined herein.
Figure 2:
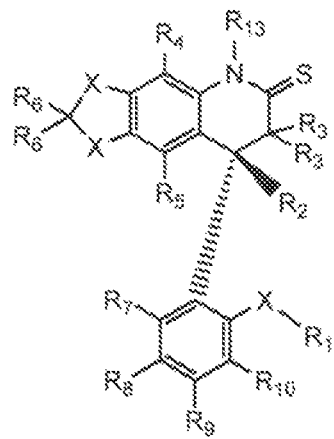
Figure 2:
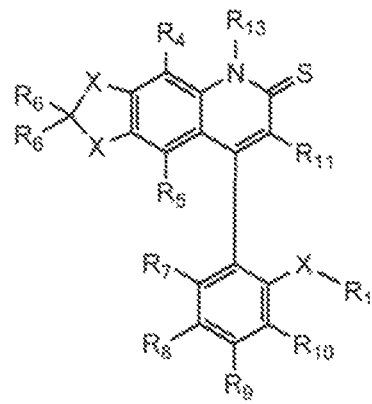
Figure 3:
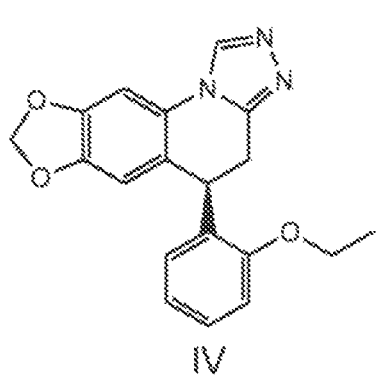
FIG. 3 is an illustration of: (i) the S-enantiomer of a triazole-containing therapeutic compound of structural formula IV; (ii) the R-enantiomer of a triazole-containing therapeutic compound of structural formula V; and (iii) a non-chiral triazole-containing therapeutic compound of structural formula VI.
Figure 3:
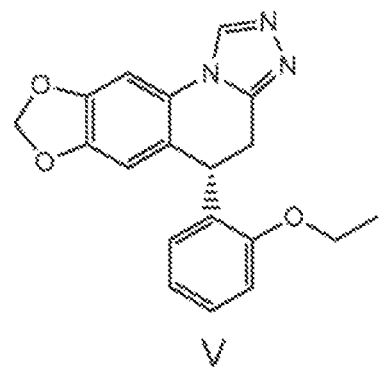
Figure 3:
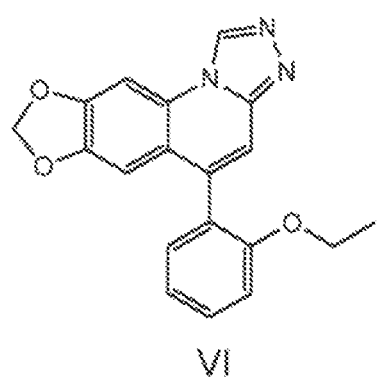
Figure 4:
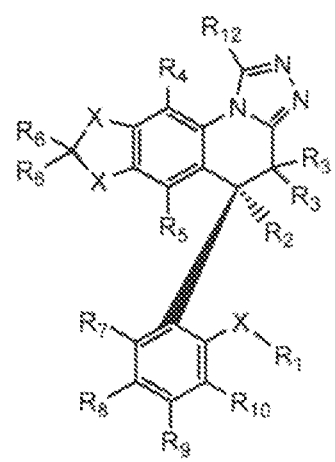
FIG. 4 is an illustration of: (i) a generic structure (i.e. XIV) for the S-enantiomer of a triazole-containing therapeutic compound of structural formula IV wherein the variables $R_1$, $R_2$, $R_3$, $R_4$, $R_5$, $R_6$, $R_7$, $R_8$, $R_9$, $R_{10}$ and $R_{12}$ are defined herein; (ii) a generic structure (i.e. XV) for the R-enantiomer of a triazole-containing therapeutic compound of structural formula V wherein the variables $R_1$, $R_2$, $R_3$, $R_4$, $R_5$, $R_6$, $R_7$, $R_8$, $R_9$, $R_{10}$ and $R_{12}$ are defined herein, (iii) a generic structure (i.e. XVI) for a non-chiral triazole-containing therapeutic compound of structural formula VI wherein the variables $R_1$, $R_4$, $R_5$, $R_6$, $R_7$, $R_8$, $R_9$, $R_{10}$, $R_{11}$ and $R_{12}$ are defined herein.
Figure 4:
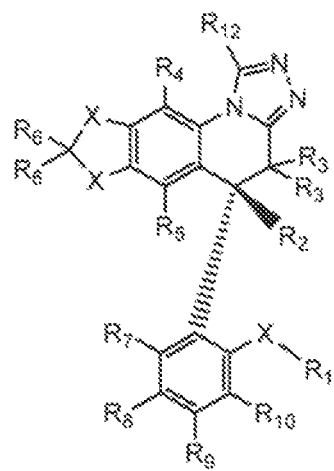
Figure 4:
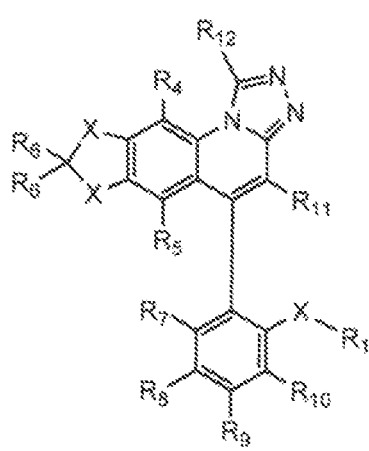

All literature and similar materials cited in this application, including but not limited to patents, patent applications, articles, books and treatises, regardless of the format of such literature or similar material, are expressly incorporated by reference herein in their entirety for any and all purposes.

DESCRIPTION

1. Field

The present invention relates generally to methods, compounds and compositions for treatment of cancer, e.g. hepatocellular carcinoma (HCC). In some embodiments, the invention relates to the use of small-molecule compounds to inhibit expression of the transcription factor Late SV40 Factor (LSF) for treatment of HCC or other cancer types.

2. Introduction

Hepatocellular carcinoma (HCC) is a primary malignant tumor, which develops in the liver. HCC is one of the five most common cancers and the third leading cause of cancer deaths worldwide. The incidence of HCC is increasing despite a decrease in overall incidence of all cancers. In the United States, the estimated new cases of HCC for 2008 were 21,370, of which 18,410 were expected to die. There are multiple etiologies, with subcategories displaying distinct gene expression profiles. The prognosis of HCC remains poor. The mean 5-year survival rate is less than 10%. The mortality rate of HCC parallels that of its incidence because HCC is a tumor with rapid growth and early vascular invasion that is resistant to conventional chemotherapy, and only a single systemic therapy (sorafenib) is available for advanced disease, although the survival benefit averages only a few months.

Hepatocellular carcinoma (HCC) is characterized by late stage diagnosis and a poor prognosis for treatment, usually consisting of surgical resection of the tumor and chemotherapy[5-7]. Currently, the only approved treatment for primary malignancies is sorafenib, a receptor tyrosine kinase and Raf inhibitor originally developed for primary kidney cancer that is also marginally effective against HCC, increasing survival by 2-3 months as a single treatment.

The current treatment options for HCC are not optimal, especially following metastasis. Irradiation and chemotherapies have not so far proved to be satisfactory; surgery is the most effective treatment of HCC. However, surgery is only appropriate for patients with small resectable tumors. Only a single, molecularly based drug (Sorafenib), which targets tyrosine kinase receptors and the MEK/ERK pathway, has generated responses in patients as a single therapy. However, increased survival times with this drug are only a few months. As such, it is imperative to discover novel, effective, and targeted therapies for this highly aggressive cancer.

The transcription factor LSF, a member of a small family of transcription factors conserved throughout the animal kingdom[15] is ubiquitously expressed in mammalian tissues and cell lines[14] LSF activity is tightly controlled as cells progress from quiescence into DNA replication (G0 to S)[3, 13] and it is required for efficient progression of cells through the G1/S transition[1, 12] Regulation of LSF activity normally occurs via post-translational modifications, with LSF protein levels generally being low and constant. However, LSF protein levels were recently shown to be highly upregulated in tumor cells, particularly in HCC cell lines and HCC patient samples[4, 16] These elevated LSF levels were shown to promote oncogenesis in the HCC cells. Based on work performed by others and by the Applicants of this submission, it is believed that there is a correlation between inhibition of LSF and remediation of HCC in a subject.

3. Definitions

For the purposes of interpreting this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise", "comprises", "comprising" "include", "includes", and "including" are interchangeable and not intended to be limiting. Furthermore, where the description of one or more embodiments uses the term "comprising", those skilled in the art would understand that in some specific instances, an embodiment or embodiments can be alternatively described using language "consisting essentially of" and/or "consisting of".

As used herein the phrases "a reference sample" and "a reference level" are used interchangeably to refer to a control of the condition. For example, in the context of treatment, a reference level can be the level of a subject that is not treated. In some embodiments, a reference level in the context of diagnosis can be the level present in a normal healthy subject. In some embodiments, a reference level or sample used herein refers to the level measured at a previous time point from a subject being treated.

As used herein, the terms "administered" and "subjected" are interchangeable with respect to the treatment of a disease or disorder and both terms refer to a subject being treated with an effective dose of pharmaceutical composition comprising a compound disclosed herein by methods of administration such as parenteral or systemic administration.

As used herein, an "agent" is a chemical molecule of synthetic or biological origin. In the context of the present invention, an agent can be a molecule that can be used in a pharmaceutical composition. In some embodiments, the agent can be a chemotherapeutic agent or agents. In some embodiments, the agent can be a small molecule compound disclosed herein (e.g. a small-molecule LSF inhibitor). In some embodiments, the agent can provide a prophylactic or therapeutic value. In some embodiments, the small molecule compounds disclosed herein can be used as a preventative or prophylactic treatment for prevention of cancer, e.g., where a subject is at risk or is likely to develop cancer. In some embodiments, the agent can be used solely to implement the invention, e.g. by formulating the small molecule compounds disclosed herein into compositions that may (or may not) further comprise a pharmaceutically acceptable carrier.

As used herein, the term "aliphatic" refers to any of the straight, branched, or cyclic alkyl, alkenyl, and alkynyl moieties as defined herein. When used herein the "aliphatic" group may be substituted or unsubstituted.

As used herein, the term "alkenyl" refers to: (i) a straight chained or branched C2 to C10 (i.e. a carbon chain from 2 to 10 carbons in length) hydrocarbon; or (ii) a cyclic C3 to C8 hydrocarbon (i.e. a carbon chain from 2 to 8 carbons in length); that comprises one or more double bonds. When used herein, the "alkenyl" group may be substituted or unsubstituted. The term "alkenyl" is also intended to refer to those compounds wherein one or more methylene groups, if any, in an alkyl chain of the alkenyl group can be replaced by a heteroatom such as —O—, —Si— or —S—. In some embodiments, alkenyl groups can be straight chained or branched C2 to C6 (i.e. a carbon chain from 2 to 6 carbons in length) hydrocarbons or cyclic C3 to C6 (i.e. a carbon chain from 3 to 6 carbons in length) hydrocarbons that comprise one or more double bonds. In some embodiments, alkenyl groups can be straight chained or branched C2 to C4 (i.e. a carbon chain from 2 to 4 carbons in length) hydrocarbons or cyclic C3 to C5 (i.e. a carbon chain from 3 to 5 carbons in length) hydrocarbons that comprise one or more double bonds.

As used herein, the term "alkenylene" refers to an alkenyl group that comprises two points of attachment to at least two moieties. When used herein the "alkenylene" group may be substituted or unsubstituted. The term "alkenylene" is also intended to refer to those compounds wherein one or more methylene groups, if any, in an alkyl chain of the alkenylene group is replaced by a heteroatom such as —O—, —Si— or —S—.

As used herein, the term "alkoxy" refers to a group represented by the formula: —O—R', wherein R' is alkyl, alkenyl, alkynyl or arylalkyl.

As used herein, the term "alkyl" refers to: (i) a straight chained or branched C2 to C10 hydrocarbon; or (ii) a cyclic C3 to C7 hydrocarbon (i.e. a carbon chain from 2 to 7 carbons in length such as a cyclopropyl group, a cyclobutyl group, a cyclopentyl group, a cyclohexyl group or a cyclohexylmethylene group); that can be completely saturated. When used herein, the "alkyl" group may be substituted or unsubstituted. The term "alkyl" is also intended to refer to those compounds wherein one or more methylene groups in the alkyl chain can be replaced by a heteroatom such as —O—, —Si— or —S—. In some embodiments, alkyl groups can be straight chained or branched C2 to C6 hydrocarbons or cyclic C3 to C6 hydrocarbons that can be completely saturated.

As used herein, the term "alkylene" refers to a straight or branched alkyl chain, arylalkyl chain or a cyclic alkyl moiety that comprises at least two points of attachment to at least two moieties (e.g., {—CH$_2$—} (methylene), {—CH$_2$CH$_2$—} (ethylene), etc., wherein the brackets indicate the points of attachment. When used herein the "alkylene" group may be substituted or unsubstituted. The term "alkylene" is also intended to refer to those compounds wherein one or more methylene groups in an alkyl chain of the alkylene group can be replaced by a heteroatom such as —O—, —Si— or —S—. In some embodiments, an alkylene group can be a C1 to C10 hydrocarbon. In some embodiments, an alkylene group can be a C1 to C6 hydrocarbon. In some embodiments, an alkylene group can be a C1 to C4 hydrocarbon.

As used herein, the term "alkynyl" refers to: (i) a straight chained or branched C2 to C10 hydrocarbon; or (ii) a cyclic C3 to C8 hydrocarbon; that comprises one or more triple bonds. When used herein, the "alkynyl" group may be substituted or unsubstituted. The term "alkynyl" is also intended to refer to those compounds wherein one or more methylene groups, if any, in an alkyl chain of the alkynyl group can be replaced by a heteroatom such as —O—, —Si— or —S—. In some embodiments, alkynyl groups can be straight chained or branched C2 to C6 hydrocarbons or cyclic C3 to C6 hydrocarbons that have one or more triple bonds. In some embodiments, alkynyl groups can be straight chained or branched C2 to C4 hydrocarbons or cyclic C3 to C5 hydrocarbons that have one or more triple bonds.

As used herein, the term "alkynylene" refers to an alkynyl group that comprises two points of attachment to at least two moieties. When used herein the "alkynylene" group may be substituted or unsubstituted. The term "alkynylene" is also intended to refer to those compounds wherein one or more methylene groups, if any, in an alkyl chain of the alkynylene group can be replaced by a heteroatom such as —O—, —Si— or —S—. In some embodiments, an alkynylene group can be a C1 to C10 hydrocarbon. In some embodiments, an alkynylene group can be a C1 to C6 hydrocarbon. In some embodiments, an alkynylene group can be a C1 to C4 hydrocarbon.

As used herein, the term "aryl", either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1 naphthyl, 2 naphthyl, 1 anthracyl, 2 anthracyl, etc.) or in which a carbocyclic aromatic ring is fused to one or more carbocyclic non aromatic rings (e.g., tetrahydronaphthylene, indan, etc.). As used herein, the "aryl" group may be substituted or unsubstituted. Aryl groups may comprise up to 30 carbon atoms and typically will comprise one or more 6 membered aromatic rings.

As used herein, the term "arylene" refers to an aryl or heteroaryl group that comprises at least two points of attachment to at least two moieties (e.g., phenylene, etc.). The point of attachment of an arylene fused to a carbocyclic, non aromatic ring may be on either the aromatic, non aromatic ring. As used herein, the "arylene" group may be substituted or unsubstituted.

As used herein, the term "arylalkyl" refers to an aryl or heteroaryl group that is attached to another moiety, such as an alkyl group or an aryl group, via an alkylene linker. As used herein, the "arylalkyl" group may be substituted or unsubstituted. The term "arylalkyl" is also intended to refer to those compounds wherein one or more methylene groups in the alkyl chain of the arylalkyl group can be replaced by a heteroatom such as —O—, —Si— or —S—.

As used herein, the term "arylalkylene" refers to an arylalkyl group that has at least two points of attachment to at least two moieties. The points of attachment can be on either the aromatic ring or the alkylene group. As used herein, the "arylalkylene" group may be substituted or unsubstituted. The term "arylalkylene" is also intended to refer to those compounds wherein one or more methylene groups, if any, in the alkyl chain of the arylalkylene group can be replaced by a heteroatom such as —O—, —Si— or —S—. When an arylalkylene is substituted, the substituents may be on either or both of the aromatic ring or the alkylene portion of the arylalkylene.

As used herein, the term "benzyl" refers to a group of formula:

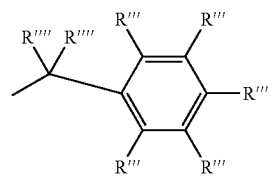

wherein each R''' is independently hydrogen, fluorine, chlorine, bromine, iodine or a methyl, ethyl, methoxy or ethoxy group and each R'''' is independently hydrogen, fluorine, chlorine, bromine, iodine or a methyl or ethyl group. In an unsubstituted benzyl group each R''' and each R'''' is independently hydrogen.

As used herein, the terms "cancer" and "malignancy" are used interchangeably and refer to a disease or disease state that is characterized by uncontrolled, abnormal growth of cells. Cancer cells can spread locally or through the bloodstream and lymphatic system to other parts of the body. The term 'cancer' is also intended to include any disease of an organ or tissue in a subject that is characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) that have migrated to other locations in the subject to establish new tumors at such locations. A small molecule compound as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition of tumor growth is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell).

As used herein a "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer may be associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness or tumor growth in suitable animal hosts such as nude mice, and the like, in vitro, in vivo, and ex vivo (see also Freshney, Culture of Animal Cells: A Manual of Basic Technique (3rd ed. 1994)).

As used herein, the terms "cellular LSF activity" and "biological activity of LSF" are used herein interchangeably. Both terms refer to the ability of LSF to regulate cellular processes downstream of LSF, for example, to modulate the expression of genes that are downstream of LSF. In some embodiments, the biological activity of LSF can elicit a stimulatory effect on expression of LSF-downstream genes. In other embodiments, the biological activity of LSF can induce an inhibitory effect on expression of LSF-downstream genes. In yet other embodiments, the biological activity of LSF may be due to interactions with other cellular proteins.

As used herein, the term "derivative" refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

As used herein, the terms "disorder" and "disease" are used interchangeably and refer to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In some embodiments, the disorder or disease is cancer. In some embodiments, the disease or disorder is liver cancer, e.g., hepatocellular carcinoma (HCC). In some embodiments, the disease or disorder is a cancer selected from the group selected from: colon cancer, breast cancer, ovarian cancer, melanoma, endometrium cancer, pancreatic cancer, prostate cancer, bone cancer, kidney cancer, leukemia, large intestine cancer, lung cancer, small cell lung carcinoma (SSLC), stomach cancer and other cancers.

As used herein, "efficacy" of a therapeutic agent refers to the relationship between a minimum effective dose and an extent of toxic side effects. Efficacy of an agent is increased if a therapeutic end point can be achieved by administration of a lower dose or a shorter dosage regimen. If toxicity can be decreased, a therapeutic agent can be administered on a longer dosage regimen or even chronically with greater patient compliance and improved quality of life. Further, decreased toxicity of an agent enables the practitioner to increase the dosage to achieve the therapeutic endpoint sooner, or to achieve a higher therapeutic endpoint.

For example, development of a cancer tumor can be evaluated by the quantitative measurement of tumor growth in terms of doubling or quadrupling tumor volume after a certain period of time. "Efficacy" of a therapeutic agent, for this example, can be determined with reference to the amount of time it takes for the tumor to double or quadruple in size in treated animals (an average number of days for doubling or quadrupling tumor size) compared to untreated animals (control).

As used herein the term "effective amount" refers to the amount of at least one therapeutic agent (e.g. small molecule compound) or pharmaceutical composition (e.g. a formulation) that can be administered to reduce or stop at least one symptom of the abnormal proliferation, for example a symptom of a cancer or malignancy. For example, an effective amount using the methods as disclosed herein may be considered as the amount sufficient to reduce a symptom of the abnormal proliferation, for example at least one symptom of a cancer (e.g. HCC) or malignancy by at least 10%. An effective amount as used herein may also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" refers to the amount of therapeutic agent (e.g. at least one small molecule compound of structural formula (I) to (X) as disclosed herein) of pharmaceutical composition to alleviate at least some of the symptoms of cancer e.g. HCC. Stated another way, "therapeutically effective amount" of a small molecule compound as disclosed herein is the amount of compound that exerts a beneficial effect on, for example, cancer, e.g., HCC in a subject to which the compound is administered. Beneficial effects may include inhibition or delay of cancer, e.g., HCC progression. The dosage administered, as single or multiple doses, to an individual will vary depending upon a variety of factors, including pharmacokinetic properties of a small molecule compound, the route of administration, conditions and characteristics (sex, age, body weight, health, size) of subjects, extent of symptoms, concurrent treatments, frequency of treatment and the effect desired.

As used herein the term "enantiomer" refers to a pair of molecular isomers which are mirror images of each other and non-superimposable. Enantiomers can differ from each other with respect to their interaction with plane-polarized light and with respect to biological activity.

As used herein, the term "expression" refers to the amount of the protein obtained by translation of RNA transcribed from a gene, and/or the amount of RNA transcribed from a gene.

As used herein, "halogen" means fluorine, chlorine, bromine, or iodine.

As used herein, the term "heteroaryl," refers to an aromatic heterocyclic ring that comprises 1, 2, 3 or 4 heteroatoms selected, independently of the others, from nitrogen, sulfur and oxygen. As used herein, the "heteroaryl" group may be substituted or unsubstituted. A heteroaryl may be fused to one or two rings, such as a cycloalkyl, an aryl, or a heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted.

As used herein, the term "heterocyclic ring" refers to any cyclic molecular structure comprising atoms of at least two different elements in the ring or rings. Additional reference is made to: Oxford Dictionary of Biochemistry and Molecular Biology, Oxford University Press, Oxford, 1997 as evidence that heterocyclic ring is a term well-established in field of organic chemistry.

As used herein, the term "hydroxyl" refers to an —OH group.

As used herein, the term "HIV" refers to the Human Immunodeficiency Virus.

As used herein, the phrase "level of LSF" as used herein encompasses the expression and/or biological activity of LSF.

As used herein, the term "LSF" is short for late SV40 factor or late Simian Virus 40 factor, and is also known as aliases LBP-1 (leader binding protein-1), LBP-1c, LBP-1d, SEF (SAA3 enhancer factor), TFCP2 (transcription factor CP2) and CP2. LSF regulates diverse cellular and viral promoters. For the purposes of this disclosure, the term "LSF" refers to a transcription factor encoded by the gene TFCP2. LSF is a DNA-binding transcription factor that is required in multiple cell types for cell cycle progression. It binds to the alpha-globin promoter and activates transcription of the alpha-globin gene. It has been reported that LSF facilitates entry into G1/S phase of the cell cycle, promotes DNA synthesis, and functions as an antiapoptotic factor.

As used herein, the phrase "level of LSF" encompasses the expression and/or biological activity of LSF.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. LSF, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, the small-molecule LSF inhibitors as disclosed herein decrease the activity or expression of LSF. Preferably, this decrease is at least about 5%, at least about 10%, at least about 25%, at least about 50%, at least about 75%, at least about 80%, or even at least about 90% of the level of expression or activity under control conditions. The term "level" as used herein in reference to LSF refers to expression or activity of LSF.

As used herein, the term "inhibit LSF" as used herein refers to inhibiting expression (level) of LSF and/or biological activity of LSF. In some embodiments, the term "inhibit LSF" refers to a decrease in the protein level of LSF and/or gene transcript level of LSF. For example, inhibition of LSF can result in a reduction in the gene expression of TFCP2 encoding LSF. The term "inhibit LSF" also refers to a down-regulation or an inhibition of biological activity of LSF, e.g. the function of LSF to modulate expression of LSF-regulated downstream genes such as genes such as thymidylate synthase (TYMS)[1], secreted phosphoprotein 1 (SPP1)[4], the complement factor H (CFH) and fibronectin 1 (FN1)[11].

As used herein the terms "inhibitors of LSF" and "LSF inhibitors" are used interchangeably and generally refer to agents that inhibit LSF. Said agents can be of synthetic or biological origins. They can be organic, or inorganic molecules, or peptides, antibodies or antisense RNA that inhibit LSF. Small molecule compounds disclosed herein can inhibit expression of LSF and/or biological activity (level) of LSF (e.g. Compounds of structural formula I, II, III, IV, V, VI, VII, VIII, IX and X). In some embodiments, the LSF inhibitors are isolated enantiomers of the compounds. In some embodiments, the LSF inhibitors are prodrugs, derivatives and/or pharmaceutically acceptable salts thereof.

As used herein, a "metastatic" cell refers to a cell that has a potential for metastasis and, when used in a method of the invention, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, as described herein, can be considered to be highly metastatic cells. Metastatic cells can be generated in a variety of ways, which are discussed further below.

As used herein the term "normal healthy subject" refers to a subject who has no symptoms of any diseases or disorders, or who is not identified with any diseases or disorders, or who is not on any medication treatment, or a subject who is identified as healthy by physicians based on medical examinations.

As used herein, the terms "optionally substituted" and "substituted or unsubstituted" are equivalent and interchangeable and refer to an alkyl, an alkylene, an alkenyl, an alkenylene, an alkynyl, an alkynylene, an aryl, an arylalkyl, an arylene, a heteroaryl or an arylalkylene group comprising one or more substituents. Suitable substituents for any an alkyl, an alkylene, an alkenyl, an alkenylene, an alkynyl, an alkynylene, an aryl, an arylalkyl, an arylene, a heteroaryl or an arylalkylene group includes any substituent that is stable under the reaction conditions used in embodiments of this invention. Non limiting examples of suitable substituents can include: an alkyl (e.g., methyl, ethyl, n-propyl, isopropyl, n-butyl, isobutyl, sec butyl, t-butyl, cyclohexyl, etc.) group, a haloalkyl (e.g., trifluoromethyl, 2,2,2-trifluoroethyl-, etc.) group, an alkoxy (e.g., methoxy, ethoxy, etc.) group, an aryl (e.g., phenyl) group, an arylalkyl (e.g., benzyl) group, a nitro group, a cyano group, a quaternized nitrogen atom or a halogen group (e.g., fluorine, chlorine, bromine or iodine) group.

In addition, any portion of an alkyl, an alkylene, an alkenyl, an alkenylene, an alkynyl, an alkynylene, an aryl, an arylalkyl, an arylene, a heteroaryl or an arylalkylene group may also be substituted with =O and/or =S.

As used herein the phrases "parenteral administration" and "administered parenterally" refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation.

As used herein, a "pharmaceutical composition" refers to a chemical or biological composition suitable for administration to a subject (e.g. human or mammal). Such compositions may be specifically formulated for administration via one or more of a number of routes, including but not limited to, oral, parenteral, intravenous, intraarterial, intraperitoneal, subcutaneous, intranasal, sublingual, intraspinal, intracerebroventricular, and the like.

As used herein, the phrase "pharmaceutically acceptable" refers to those compounds, materials, compositions, formulations and/or dosage forms which are, within the scope of sound medical judgment, suitable for use in contact with the tissues of human beings and/or animals without excessive toxicity, irritation, allergic response, or other problem or complication, commensurate with a reasonable benefit/risk ratio.

As used herein, the phrase "pharmaceutically acceptable carrier" refers to a pharmaceutically acceptable material, composition or vehicle, such as a liquid or solid filler, diluent, excipient, solvent or encapsulating material, involved in carrying or transporting the subject agents (e.g. small molecule compounds I-X) from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert or substantially inert. The terms "physiologically tolerable carriers" and "biocompatible delivery vehicles" are sometimes used in the literature or herein and are intended to be interchangeable with the phrase "pharmaceutically acceptable carrier".

As used herein, the term "phenoxy" refers to a phenolic group represented by the formula: —O—R", wherein R" is aryl or heteroaryl.

As used herein, the term "phenyl" refers to a group of formula:

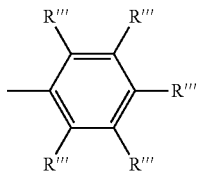

wherein each R''' is independently, hydrogen, fluorine, chlorine, bromine, iodine or a methyl, ethyl, methoxy or ethoxy group. In an unsubstituted phenyl group each R''' is hydrogen.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, a "prodrug" refers to a compound that can be converted via some chemical or physiological process (e.g., enzymatic processes and metabolic hydrolysis) to a prophylactic or therapeutic compound.

As used herein with reference to expression of a gene, the terms "regulate" and "modulate" are interchangeable and refer to producing an effect on, for example, gene expression. In some embodiments, the effect can be stimulatory, such as increasing expression of a gene. In some embodiments, the effect can be inhibitory, such as decreasing expression of a gene.

As used herein, "sarcoma" refers to a type of cancer cell that is derived from connective tissue, e.g., bone (osteosarcoma), cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

As used herein the term "subject" and "individual" are used interchangeably and include humans and animals (such as other mammalian subjects) that receive either prophylactic or therapeutic treatment. The term "subject" may, for example, refer to a human, to whom treatment, including prophylactic treatment, with compounds I-X according to the present invention, is provided. A "non-human" subject may include mammals such as rats, mice, rabbits, sheep, cats, dogs, cows, pigs, and non-human primates.

As used herein the phrases "systemic administration," "administered systemically", "peripheral administration" and "administered peripherally" are interchangeable and refer to the administration of a pharmaceutical composition comprising at least one small molecule compound of structural formula I, II, III, IV, V, VI, VII, VIII, IX, X, XI, XII, XIII, XIV, XV, XVI or XXXI as disclosed herein such that it enters the animal's system and, thus, is subject to metabolism and other like processes.

As used herein, the term "tissue" is intended to include intact cells, blood, blood preparations such as plasma and serum, bones, joints, muscles, smooth muscles, and organs. In some embodiments, the tissue can mean liver tissue.

As used herein with respect to treatment of a disease or disorder, the term "treat", "treatment" and "treating" are used interchangeably, and refer to preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is at risk thereof as well as slowing or reducing progression of existing disease. In some embodiments, treatment can be prophylactic in terms of completely or partially preventing a disease or sign or symptom thereof. For example, subjects at high risk of HCC, such as those infected with HBV or HCV, can be subjected to prophylactic treatment to prevent the onset of HCC. In some embodiments, prophylactic treatment can be administered to subjects who had prior treatment of a disease and the disease is in remission. For example, for subjects who have their HCC tumors removed or stabilized by previous therapeutic methods can be prophylactically treated (e.g. with a LSF inhibitor) to prevent the recurrence and metastasis of HCC. In other embodiments, treatment can be therapeutic in terms of eliminating or reducing at least one symptom of the condition or disease. For example, in the case of HCC, therapeutic treatment refers to inhibiting or delaying the progression of HCC in a subject that is already inflicted with HCC. Measurable lessening includes any statistically significant decline in a measurable marker or symptom, such as measuring a tumor size or level of a biomarker.

As used herein, the terms "tumor" and "tumor cell" are used interchangeably and refer to the tissue mass or tissue type of cell that is undergoing abnormal proliferation.

As used herein, a "tumorigenic cell" refers to a cell that, when introduced into a suitable site in a subject, can form a tumor. The cell may be non-metastatic or metastatic. The tumor cells may be, e.g., from cancers of breast, lung, colon, bladder, prostate, liver, gastrointestinal tract, endometrium, tracheal-bronchial tract, pancreas, liver, uterus, ovary, nasopharynges, prostate, bone or bone marrow, brain, skin or other suitable tissues or organs. Cancer cells can be of human origin.

As used herein, the terms "up-regulate", "increase" or "activate" are all used to refer to an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level. In some embodiments the increase can be greater than 100%. For example, the increase can be about a 2-fold, or about a 3-fold, or about a 4-fold, or about a 5-fold or about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

4. General

It is to be understood that the discussion set forth below in this "General" section can pertain to some, or to all, of the various embodiments of the invention described herein.

Late SV40 Factor (LSF)

LSF is a DNA-binding transcription factor that is required in multiple cell types for cell cycle progression. LSF binds to the alpha-globin promoter and activates transcription of the alpha-globin gene. It has been reported that LSF facilitates entry into G1/S phase of the cell cycle, promotes DNA synthesis, and functions as an antiapoptotic factor[1].

LSF also regulates erythroid gene expression, plays a role in the transcriptional switch of globin gene promoters, and activates many other cellular and viral gene promoters. The gene product interacts with certain inflammatory response factors, and polymorphisms of this gene can be involved in the pathogenesis of Alzheimer's disease.

A major cellular target of LSF is the thymidylate synthase (TS) gene (TYMS), which encodes the rate-limiting enzyme in the production of dTTP, required for DNA synthesis[1]. TS has been a long-standing chemotherapeutic target for cancer treatments, and recently it was discussed that elevated levels of LSF in hepatocellular carcinoma cell lines can contribute to chemoresistance to one commonly utilized thymidylate synthetase inhibitor, 5-fluorouracil.[4] Inhibition of LSF abrogates TS induction, induces either arrest at the G1/S transition, or in apoptosis after entry into S phase. Thus, LSF plays an important role in DNA synthesis and cell survival.

In the liver, LSF is activated by inflammatory cytokines and regulates the expression of acute phase proteins[8,9].

Inhibitors of LSF

The ability of a compound to inhibit LSF can be assessed by measuring a decrease in expression or activity (level) of LSF as compared to the level of LSF in the absence of inhibitors of LSF. In some embodiments, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor can inhibit biological activity of LSF, such as a decrease in expression of SPP1 that encodes osteopontin (OPN, also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

In some embodiments, the ability of a compound to inhibit LSF is assessed by inhibition of LSF-induced tumorigenesis and metastasis of cancer cells, e.g. hepatocellular carcinoma cells in vitro or in an in vivo animal model as demonstrated in the Examples herein, as compared to a reference condition without treatment with such a LSF inhibitor. In such embodiments, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

The present invention relates in part to small molecule compounds as well as related compositions and methods directed to LSF inhibitors. In some embodiments, small molecule inhibitors of LSF, as disclosed herein, can be used to inhibit the cellular LSF activity. In some embodiments, LSF inhibitors as disclosed herein can decrease expression (level) of LSF.

One of the major targets of LSF is thymidylate synthase (TS) gene (TYMS), which encodes the rate-limiting enzyme in the production of dTTP, required for DNA synthesis[1].

Additional examples of LSF-downstream genes are disclosed in Yoo et al, PNAS, 2010, 107; 8357-8362, and include without limitation SPP1 (encoding osetopontin), complement factor H (CFH), TSPAN8, S100A10, CDH17, EFNB2, ZEB1, REG1A, REG3A, SAA4, TAGLN, FGFR2, EGFR, CYP2B7P1, CYP2B6, GPX2, DPYD, PKLR, LEF1, ICAM2 and IGFBP7.

In some embodiments, the genes downstream of LSF are tumor-associated genes, such as relating to invasion and metastasis, angiogenesis, epithelial-mesenchymal transition (EMT), cell growth, drug metabolism, senescence, cell adhesion, glycolysis, Wnt signaling, growth and regeneration, inflammatory response, e.g. acute phase proteins, and modulators of matrix-degrading enzymes e.g. MMP9. In various embodiments, LSF is a transcription factor encoded by TFCP2. Thus, inhibiting LSF can disrupt or inhibit LSF binding to DNA and/or interaction of LSF with other proteins to form a complex.

Accordingly, in some embodiments, inhibition of cellular LSF activity can be determined by measuring the level of downstream genes regulated by the transcription factor LSF. The effect of LSF on expression (level) of LSF-targeted or LSF-downstream genes can be stimulatory or inhibitory. For example, one gene induced by LSF is SPP1 encoding OPN. Thus, an inhibition of biological activity of LSF results in a decrease in level of SPP1 mRNA and/or a decrease in the amount of the respective encoded protein, OPN. In another embodiment, one gene inhibited downstream of LSF is TAGLN. Thus, an inhibition of biological activity of LSF leads to an increase in level of TAGLN mRNA. In some embodiments, the cellular activity of LSF can be measured by a reduction in the level of TS.

In further embodiments, inhibition of LSF can decrease expression of LSF, for example, a reduction in protein level, and/or a decrease in gene transcript level (e.g. mRNA) of LSF.

One aspect of the present invention provides methods of identifying inhibitors of LSF, for example, by the method comprising measuring the LSF activity in a LSF-dependent luciferase reporter assay as described in Yoo et al.[4]. As disclosed herein, inhibitors of LSF can decrease functional transcriptional activity or the expression of LSF (e.g., such as protein level of LSF, and/or gene transcript level of LSF), by at least about 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. The expression of LSF can be measured by standard methods known to an skilled artisan such as western blot, ELISA, and quantitative PCR as well as the methods provided in the Examples section below.

In some embodiments, inhibitors of LSF as disclosed herein can inhibit or decrease cellular LSF activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%.

In some embodiments, small molecule inhibitors of LSF can decrease expression of downstream genes up-regulated by LSF, e.g. SPP1 encoding OPN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. In alternative embodiments, inhibitors of LSF can increase expression of downstream genes down-regulated by LSF, e.g. TAGLN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF.

Examples of such small molecule LSF inhibitors include compounds of structural formula I, II, III, IV, V, VI, VII, VIII, IX, X, XI, XII, XIII, XVI, XVII, XVIII and XXX (as defined herein).

A Link Between LSF and Cancer

A recent publication has demonstrated a link between LSF and cancer (particularly HCC)[4]. Indeed, the authors claim that LSF has a regulatory role in cancer (and HCC in particular) and inhibition of LSF is a viable target for therapeutic intervention. Thus, small molecule inhibitors of LSF may be effective as prophylactic or therapeutic agents. Consequently, small molecule LSF inhibitors such as compounds of structural formula I, II, III, IV, V, VI, VII, VIII, IX, X, XI, XII, XIII, XVI, XVII, XVIII and XXX (as defined herein) are possible prophylactic or therapeutic agents for treatment of cancer (e.g. HCC)

Prodrugs:

A prodrug may be inactive when administered to a subject, i.e. an ester, but is converted in vivo to an active compound, for example, by hydrolysis to the free carboxylic acid or free hydroxyl. A prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Some examples of prodrugs include compounds wherein a hydroxy, amino or mercapto group is bonded to any group that, when the prodrug of the active compound is administered to a subject, the group cleaves to form a free hydroxy, free amino or free mercapto group, respectively. Some other examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* II:345-365; Gaignault et al. (1996) "Designing Prodrugs and Bio-precursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(I-3):63-80 (1999); Waller et al., "Prodrugs", *Br. J. Clin. Pharmac.* 28: 497-507 (1989), content of all of which is herein incorporated by reference in its entirety.

Thus, in some embodiments, this invention also pertains to prodrugs of any of compounds I, II, III, IV, V, VI, VII, VIII, IX, X, XI, XII, XIII, XVI, XVII, XVIII and XXX (as defined herein).

Assays

In some embodiments, this invention also pertains to assays such as cell assays. The cell assays can be performed on cells, cell cultures (or subcultures thereof) or with tissue such as a tumor. The source of the cell(s) or tissue(s) can be from any source. The cell(s) or tissue(s) can be normal or diseased. In some embodiments, the assay is performed to determine whether or not the cell or tissue exists in a disease state or possesses a predisposition to a disease state.

Thus, in some embodiments, this invention pertains to an assay method for treating cells (including cells of tissue) comprising contacting the cells with: (i) at least one small molecule compound (e.g. compounds I, II, III, IV, V, VI, VII, VIII, IX, X, XI, XII, XIII, XIV, XV, XVI or XXX, as defined herein); (ii) compositions, mixtures or formulations comprising said compounds; (iii) prodrugs of said compounds; or (iv) combination therapies using said compound, compositions or prodrugs. In some embodiments, the cells are sequentially, in either order, or simultaneously contacted with said compounds, compositions, mixtures or formulation, prodrugs or combination therapies. In some embodiments, the cells or tissue(s) may be contacted with various different chemotherapy agents, vitamins, antioxidant supplements and/or neutraceuticals, each at various different concentrations, to thereby determine toxic levels of the various therapeutic agents, vitamins antioxidant supplements, neutraceuticals and/or combinations thereof. In some embodiments, the cell assay may, for example, be used to confirm a disease state. In some embodiments, the cell assay may, for example, be used to monitor the progression (or not) of a disease state. Additionally, based on the results of the assay, a physician or practitioner may further decide on a treatment regime for the subject or may even customize the treatment regime based on the results of the assay (i.e. personalized medicine).

Treatments

In some embodiments, the small molecule compounds that are LSF inhibitors can be used to treat a subject. The treatment can be prophylactic or for an active disease. For example, the treatment may involve treatment of a subject having cancerous cells and/or tumors.

Thus, this invention can pertain to treating a disease state (such as a tumor) in a subject by administering to said subject: (i) at least one small molecule compound (e.g. compounds I, II, III, IV, V, VI, VII, VIII, IX, X, XI, XII, XIII, XIV, XV, XVI or XXX); (ii) compositions, mixtures or formulations comprising said compounds; (iii) prodrugs of said compounds; or (iv) combination therapies using said compound, compositions or prodrugs. The subject may be any subject. For example the subject to be a patient or other subject in a clinical setting. The subject could be a cancer patient.

Mixtures and/or formulations for the treatment of subjects may comprise pharmaceutically acceptable carriers and any other compounds or formulations deemed suitable. The specific ratios of the various compounds, other therapeutic agents and/or pharmaceutically acceptable carriers and their dosing will be determined using methods known to the skilled artisan. In general, a suitable daily dose of a particular formulation (and the individual compounds and agents contained therein) will be that amount which is the lowest dose effective to produce a therapeutic effect. However, dosing (of one or more of the compounds and/or agents) can be increased if a beneficial therapeutic effect is observed while toxic effects are avoided.

5. Various Embodiments of the Invention

It should be understood that the order of steps or order for performing certain actions is immaterial so long as the present teachings remain operable or unless otherwise specified. Moreover, in some embodiments, two or more steps or actions can be conducted simultaneously so long as the present teachings remain operable or unless otherwise specified.

Small molecule compounds disclosed herein can be used to inhibit LSF expression. Examples of such small molecule LSF inhibitors include compounds of structural formula I, II, III, IV, V, VI, VII, VIII, IX and X shown herein. Said compounds are also possible prophylactic or therapeutic agents for treatment of cancer (e.g. HCC). Thus, more generically, in some embodiments, this invention pertains to a compound of structural formula XI, XII or XIII;

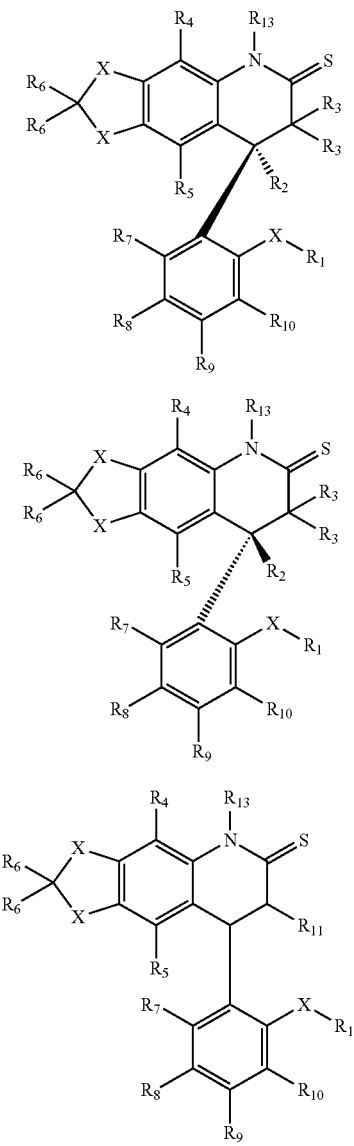

XI

XII

XIII or a pharmaceutically acceptable salt thereof wherein, each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; $R_4$, $R_5$, $R_7$, $R_8$, $R_9$, $R_{10}$ and $R_{11}$ are each independently hydrogen, fluorine, chlorine, bromine, iodine or a hydroxyl, alkoxy, phenoxy, alkyl, alkenyl, alkynyl, aryl, heteroaryl or arylalkyl group; and $R_{13}$ is hydrogen or an alkyl, alkenyl, alkynyl, aryl, heteroaryl or arylalkyl group.

In some embodiments, this invention pertains to a compound of structural formula XI, XII or XIII: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; $R_4$, $R_5$, $R_7$, $R_8$, $R_9$, $R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_{13}$ is hydrogen or methyl, ethyl, n-propyl, isopropyl, n-butyl, iso-butyl, sec-butyl, phenyl or benzyl group.

In some embodiments, this invention pertains to a compound of structural formula XI, XII or XIII: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; $R_4$, $R_5$, $R_7$, $R_8$, $R_9$, $R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_{13}$ is hydrogen, methyl or ethyl.

In some embodiments, this invention pertains to compounds of structural formula I, II or III;

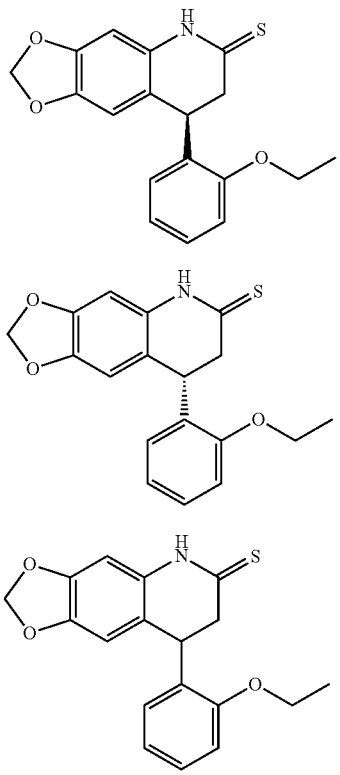

I

II

III or a pharmaceutically acceptable salt thereof.

Based on the information provided in the Examples, Compounds I, II and III exhibit properties as LSF inhibitors. Thus, said compounds should also be useful as cancer prophylactic agents and/or therapeutic agents.

Also, more generically, in some embodiments, this invention pertains to a compound of structural formula XIV, XV or XVI;

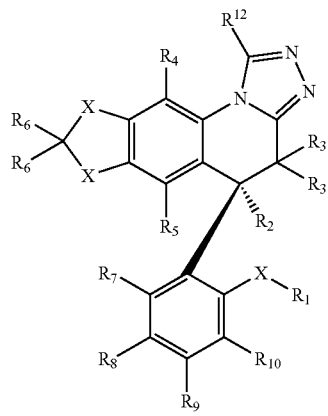

XIV

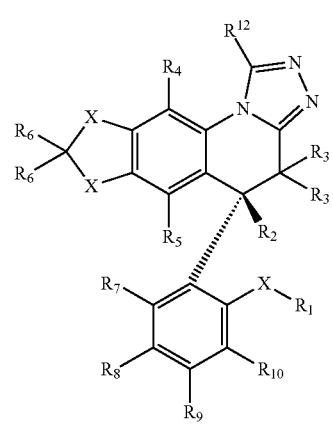

XV

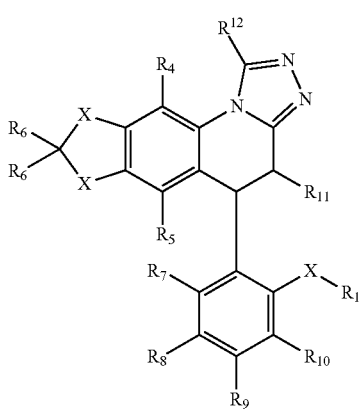

XVI or a pharmaceutically acceptable salt thereof wherein, each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

In some embodiments, this invention pertains to a compound of structural formula XIV, XV or XVI: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group.

In some embodiments, this invention pertains to a compound of structural formula XIV, XV or XVI: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group.

In some embodiments, this invention pertains to compounds of structural formula IV, V or VI;

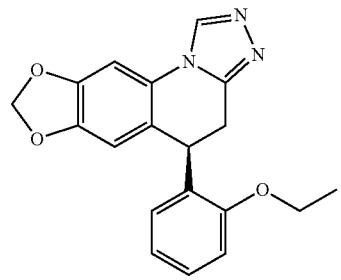

IV

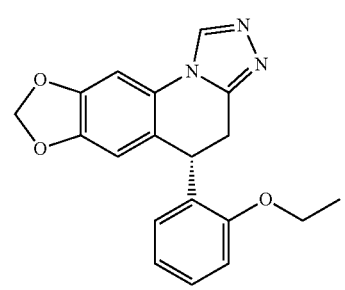

V

VI

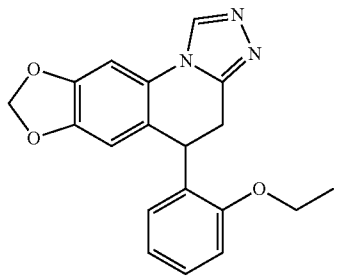

or a pharmaceutically acceptable salt thereof.

Based on the information provided in the Examples, Compounds IV, V and VI exhibit properties as LSF inhibitors. Thus, said compounds should also be useful as cancer prophylactic agents and/or therapeutic agents.

In some embodiments, this invention pertains to compositions. Such compositions can comprise one or more of the compounds described above. For example, the compositions may be formulations. Thus, in some embodiments, this invention pertains to a composition comprising a compound of structural formula XI, XII or XIII;

XI

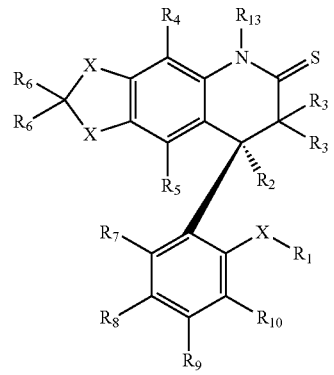

XII

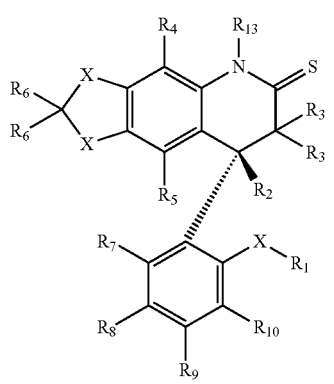

XIII

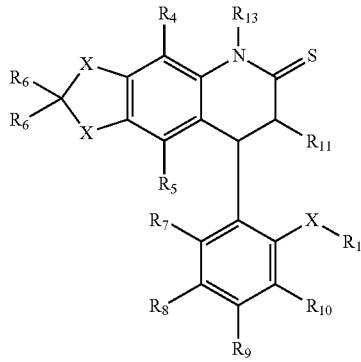

or a pharmaceutically acceptable salt thereof, wherein; each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; $R_4$, $R_5$, $R_7$, $R_8$, $R_9$, $R_{10}$ and $R_{11}$ are each independently hydrogen, fluorine, chlorine, bromine, iodine or a hydroxyl, alkoxy, phenoxy, alkyl, alkenyl, alkynyl, aryl, heteroaryl or arylalkyl group; and $R_{13}$ is hydrogen or an alkyl, alkenyl, alkynyl, aryl, heteroaryl or arylalkyl group.

In some embodiments, this invention pertains to a composition comprising one or more compounds of structural formula XI, XII or XIII: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; $R_4$, $R_5$, $R_7$, $R_8$, $R_9$, $R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_{13}$ is hydrogen or a methyl, ethyl, n-propyl, isopropyl, n-butyl, iso-butyl, sec-butyl, phenyl or benzyl group.

In some embodiments, this invention pertains to a composition comprising one or more compounds of structural formula XI, XII or XIII: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; $R_4$, $R_5$, $R_7$, $R_8$, $R_9$, $R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_{13}$ is hydrogen, methyl or ethyl.

In some embodiments, this invention pertains to compositions comprising one or more compounds of structural formula I, II or III;

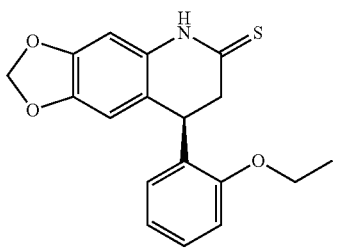

I

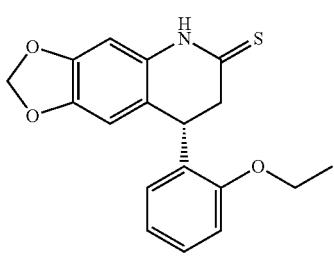

II

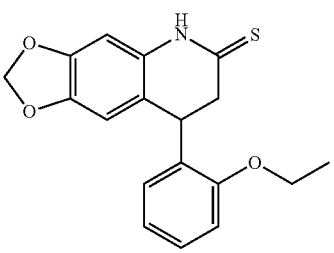

III or a pharmaceutically acceptable salt thereof.

In some embodiments, this invention pertains to a composition comprising one or more compounds of structural formula XIV, XV or XVI;

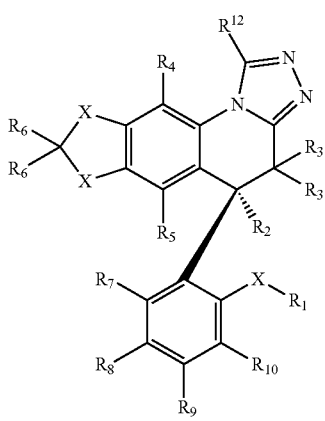

XIV

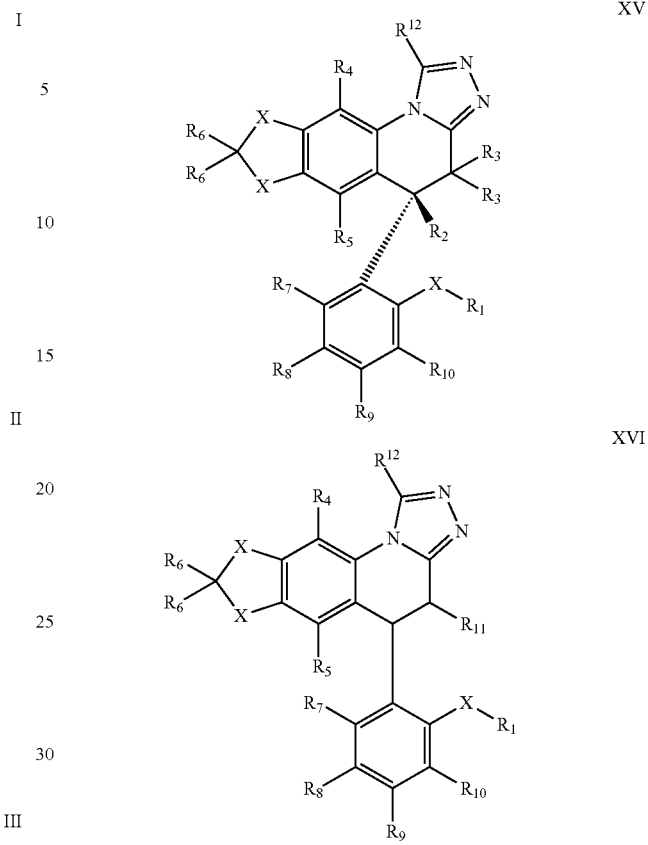

or a pharmaceutically acceptable salt thereof wherein, each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

In some embodiments, this invention pertains to a composition comprising one or more compounds of structural formula XIV, XV or XVI: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group.

In some embodiments, this invention pertains to a composition comprising one or more compounds of structural formula XIV, XV or XVI: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group.

In some embodiments, this invention pertains to compositions comprising one or more compounds of structural formula IV, V or VI:

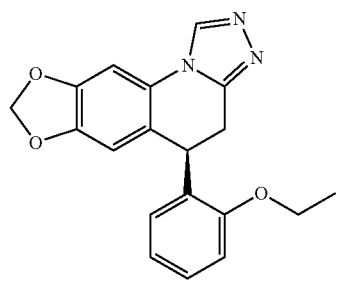

IV

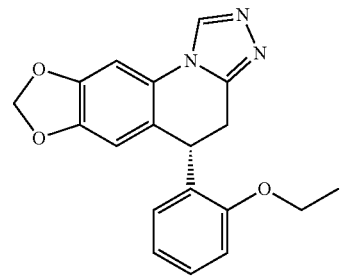

V

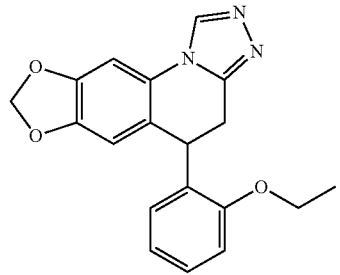

VI or a pharmaceutically acceptable salt thereof.

In some embodiments, any of the forgoing compounds and/or compositions may further comprise a pharmaceutically acceptable carrier.

As noted above, the small molecule compounds disclosed above exhibit properties as LSF inhibitors. Thus, in some embodiments, this invention pertains to a method comprising administering to a subject, to inhibit or treat LSF in said subject, an effective amount of a compound of structural formula XI, XII or XIII:

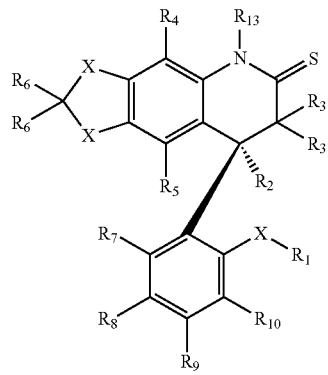

XI

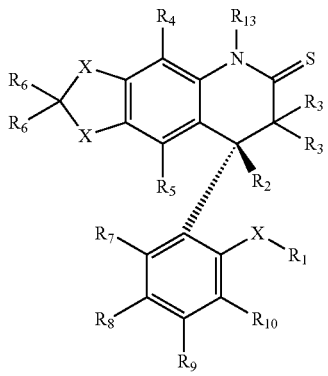

XII

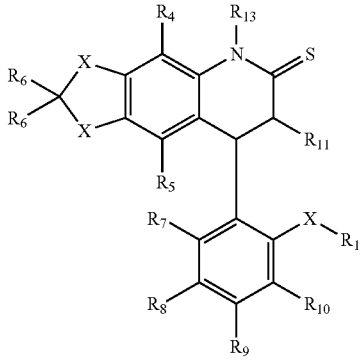

XIII or a pharmaceutically acceptable salt thereof, wherein, each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; $R_4$, $R_5$, $R_7$, $R_8$, $R_9$, $R_{10}$ and $R_{11}$ are each independently hydrogen, fluorine, chlorine, bromine, iodine or a hydroxyl, alkoxy, phenoxy, alkyl, alkenyl, alkynyl, aryl, heteroaryl or arylalkyl group; and $R_{13}$ is hydrogen or an alkyl, alkenyl, alkynyl, aryl, heteroaryl or arylalkyl group.

In some embodiments, this invention pertains to a method comprising administering to a subject, to inhibit or treat LSF in said subject, an effective amount of a compound of structural formula XI, XII or XIII: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; $R_4, R_5, R_7, R_8, R_9, R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_{13}$ is hydrogen or methyl, ethyl, n-propyl, isopropyl, n-butyl, iso-butyl, sec-butyl, phenyl or benzyl group.

In some embodiments, this invention pertains to a method comprising administering to a subject, to inhibit or treat LSF in said subject, an effective amount of a compound of structural formula XI, XII or XIII: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; $R_4, R_5, R_7, R_8, R_9, R_{10}$ and $R_{11}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_{13}$ is hydrogen, methyl or ethyl.

In some embodiments, this invention pertains to a method comprising administering to a subject, to inhibit or treat LSF in said subject, an effective amount of a compound of structural formula I, II or III:

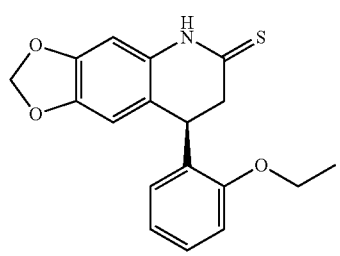

I

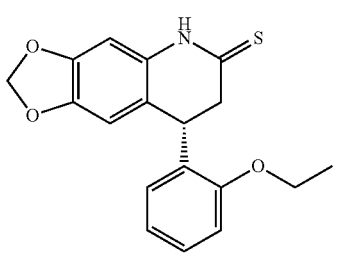

II

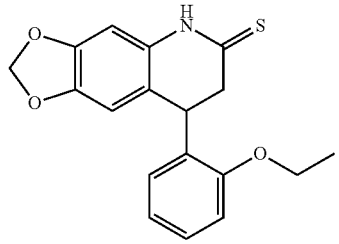

III or a pharmaceutically acceptable salt thereof.

In some embodiments, this invention pertains to a method comprising administering to a subject, to inhibit or treat LSF in said subject, an effective amount of a compound of structural formula XIV, XV or XVI;

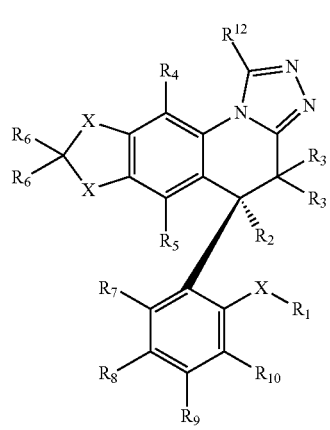

XIV

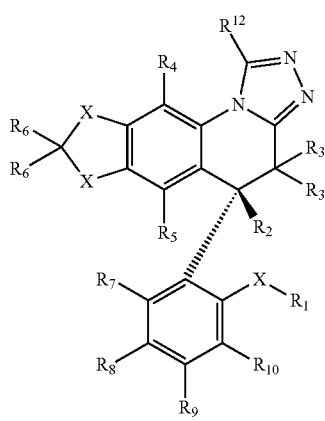

XV

-continued

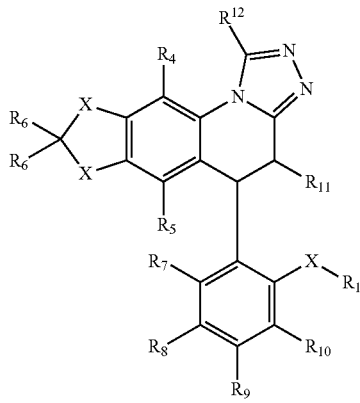

XVI or a pharmaceutically acceptable salt thereof, wherein, each X is independently O or S; $R_1$ is hydrogen or an alkyl, alkenyl, alkynyl, aryl, heteroaryl or arylalkyl group; $R_2$ is hydrogen or a hydroxyl, alkoxy, phenoxy, alkyl, alkenyl, alkynyl, aryl, heteroaryl or arylalkyl group; each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

In some embodiments, this invention pertains to a method comprising administering to a subject, to inhibit or treat LSF in said subject, an effective amount of a compound of structural formula XIV, XV or XVI: wherein each X is O or S; $R_1$ is hydrogen or a methyl, ethyl, n-propyl, isopropyl, n-butyl, iso-butyl, sec-butyl, substituted or unsubstituted phenyl or substituted or unsubstituted benzyl group; $R_2$ is hydrogen or a hydroxyl, methoxy, ethoxy, methyl, ethyl, n-propyl, isopropyl, n-butyl, iso-butyl, sec-butyl, phenyl or benzyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group.

In some embodiments, this invention pertains to a method comprising administering to a subject, to inhibit or treat LSF in said subject, an effective amount of a compound of structural formula XIV, XV or XVI: wherein each X is O or S; $R_1$ is hydrogen or a methyl, ethyl, n-propyl, isopropyl, n-butyl or iso-butyl group; $R_2$ is hydrogen or a hydroxyl, methoxy, ethoxy, methyl, ethyl, n-propyl, isopropyl, n-butyl or iso-butyl group; each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, unsubstituted phenyl or unsubstituted benzyl group.

In some embodiments, this invention pertains to a method comprising administering to a subject, to inhibit or treat LSF in said subject, an effective amount of a compound of structural formula IV, V or VI:

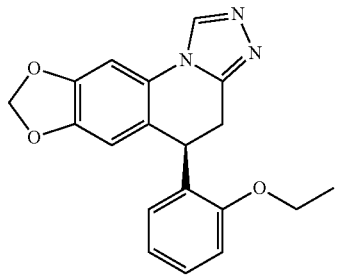

IV

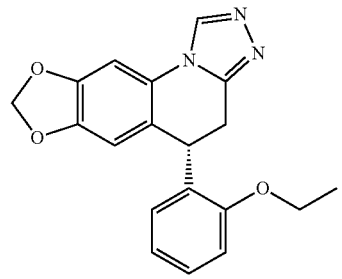

V

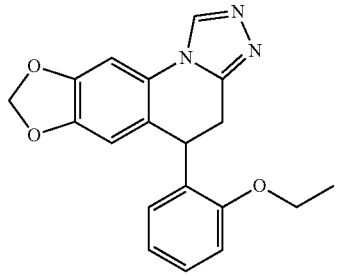

VI or a pharmaceutically acceptable salt thereof.

In any of the above described methods, said composition may further comprise a pharmaceutically acceptable carrier. In any of the above described methods, said subject may suffer from, or be at risk for, hepatocellular carcinoma. In any of the above described methods, said subject may suffer from, or be at risk for, HIV. In any of the above described methods, said subject is a mammal. In any of the above described methods, said subject may be a human.

Because they can inhibit LSF, the compounds and compositions disclosed herein can be used to prepare medicaments for the treatment of cancer. Thus, in some embodiments, this invention is directed to the use of any of the compounds or compositions herein discussed for the manufacturer of a medicament for treatment of cancer (e.g. hepatocellular carcinoma). In some embodiments, the medicament further comprises a pharmaceutical acceptable carrier. In some embodiments, the medicament further comprises at least one other therapeutic agent. In some embodiments, the medicament is used for the treatment of hepatocellular carcinoma present in a mammal. The mammal can be a human.

Similarly, because the compounds and compositions comprising said compounds disclosed herein can be used as LSF inhibitors, in some embodiments, this invention also pertains to the use of any of said compounds and/or compositions herein disclosed for the manufacture of a composition capable of inhibiting LSF in a cell or tissue.

Figure 5:
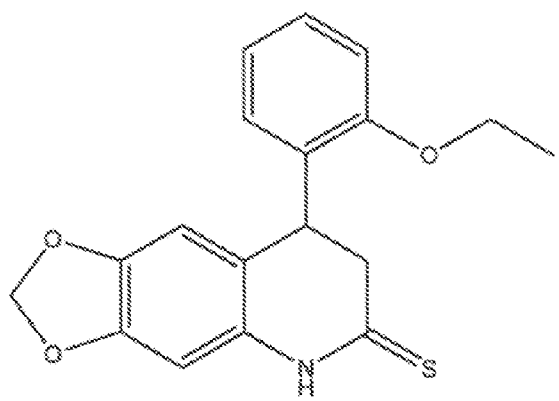
FIG. 5 is: (i) an illustration of the generic structural formula for the racemic mixture of the thio-containing therapeutic compounds of structural formulas I and II; and (ii) a graphic illustration of data for the treatment of a cell line with the racemic mixture of the thio-containing therapeutic compounds of structural formulas I and II.
Figure 5:
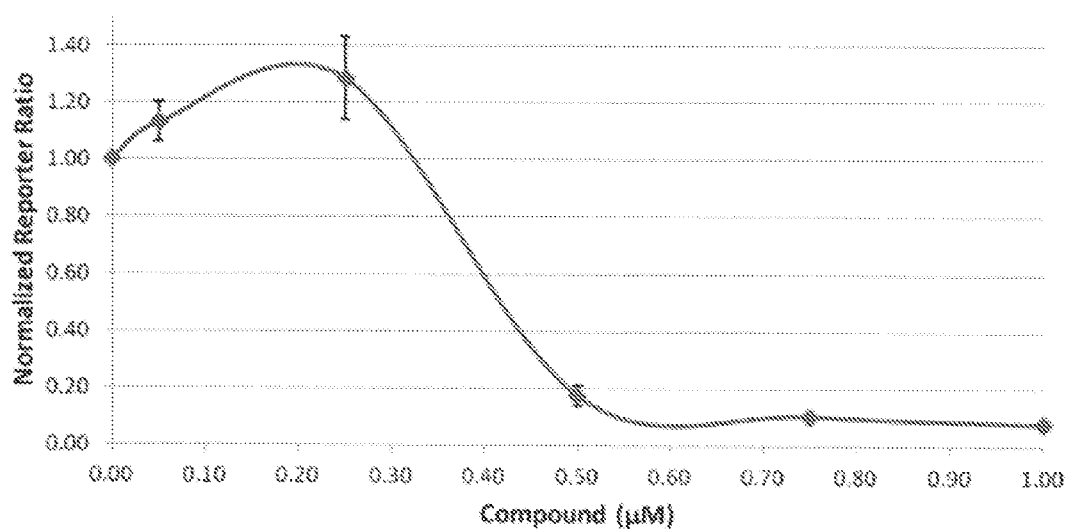
Figure 6:
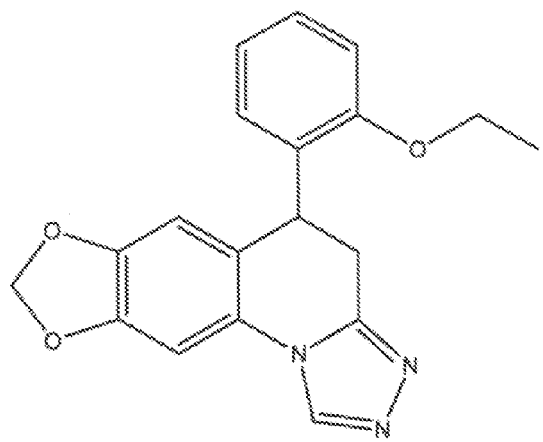
FIG. 6 is: (i) an illustration of the generic structural formula for the racemic mixture of the triazole-containing therapeutic compounds of structural formulas IV and V; and (ii) a graphic illustration of data for the treatment of a cell line with the racemic mixture of the triazole-containing therapeutic compounds of structural formulas IV and V.
Figure 6:
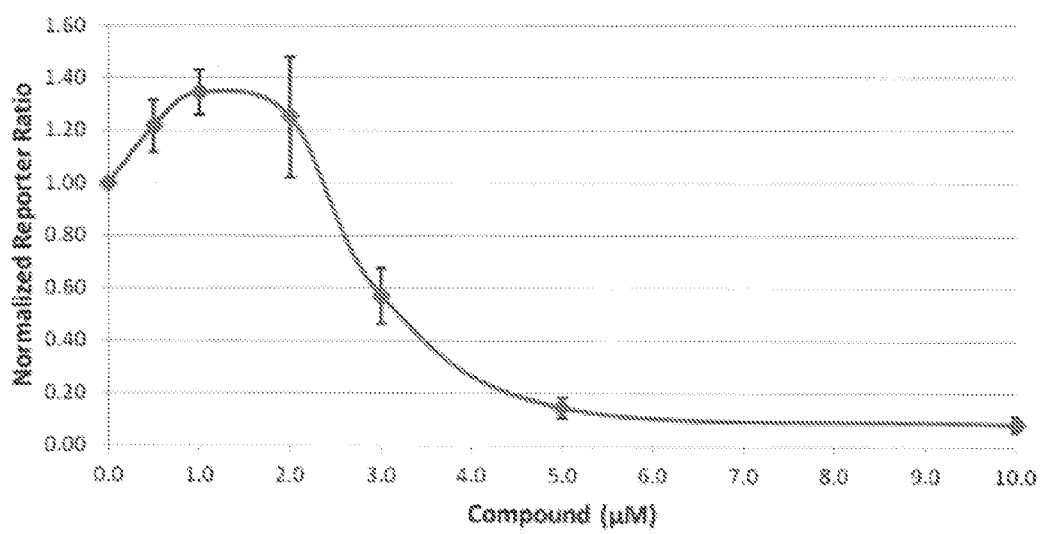
Figure 7:
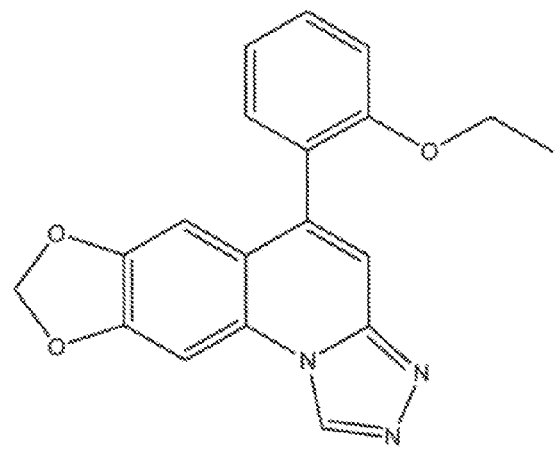
FIG. 7 is: (i) an illustration of the non-chiral triazole-containing therapeutic compound of structural formula VI; and (ii) a graphic illustration of data for the treatment of a cell line with the compound of structural formula VI.
Figure 7:
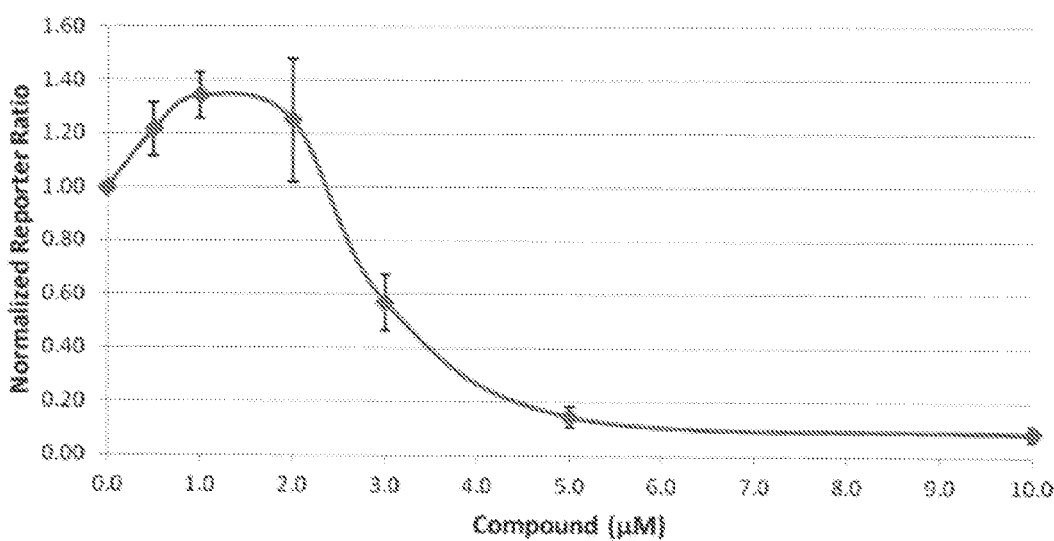

As shown in Example 10 and FIGS. 5-7, compounds and compositions disclosed herein can be used to inhibit LSF in cells. Thus, in some embodiments, this invention pertains to a method comprising: a) contacting a cancerous cell or cancerous tissue with any small molecule compound herein disclosed; and b) monitoring, directly or indirectly, the expression or activity of LSF associated with said cancerous cell or cancerous tissue. Similarly, this invention also pertains to a method comprising: a) contacting a cancerous cell or cancerous tissue with any composition comprising a small molecule compound herein disclosed; and b) monitoring, directly or indirectly, the expression or activity of LSF associated with said cancerous cell or cancerous tissue.

Various small molecule compounds (e.g. the racemic mixture of compounds I and II) are particularly strong LSF inhibitors as shown in FIG. 5. For example, this racemic mixture is about one order of magnitude (i.e. about 10 times as effective) more effective as compared with the racemic mixture of compounds IV and V (FIG. 6) and Compound VI (FIG. 7). In experiments thus far performed by the applicants, the mixture of compounds I and II is the strongest LSF inhibitor so far observed.

6. Examples

Aspects of the present teachings can be further understood in light of the following examples, which should not be construed as limiting the scope of the present teachings in any way.

Example 1

Synthesis of FQI-1 (8-(2-ethoxyphenyl)-7,8-dihydro-[1,3]dioxolo[4,5-g]quinolin-6(5H)-one)

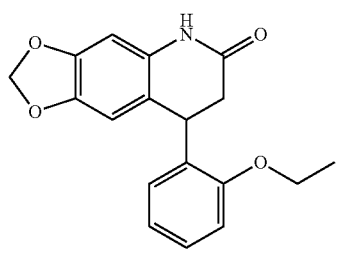

(FQI-1)

To a flame-dried 25 mL round bottom flask equipped with stir bar and back filled with argon was added 7.5 mL dimethyl formamide, 134 mg (0.7 mmol) 2-ethoxycinnamic acid, and 306 mg of N-[(dimethylamino)-1H-2,3,-triazolo-[4,5-b]pyridin-1-yl-methylene]-N-methylmethanaminiumhexafluorophosphate (HATU) (0.81 mmol, 1.15 equiv). Reaction was allowed to stir at room temperature for 1 hour and then to it was added 244 µL N,N'-diisopropylethylamine (DIPEA) (1.4 mmol, 2.0 equiv) and 112 mg methylenedioxle aniline (0.735 mmol, 1.05 equiv). Reaction was allowed to stir at room temperature for 3 hours and then to it was added 25 mL ethyl acetate (EtOAc) and 25 mL water. Organic layer was then separated and aqueous layer was washed with EtOAc (2×25 mL). Organic layers were combined and washed with brine, dried over sodium sulfate and collected via filtration. Ethyl acetate solution was then concentrated onto silica gel and purified via column chromatography with eluant 50:50 hexane:EtOAc. Fractions with desired material present as seen by UV were collected and concentrated to give 230 mg desired acrylamide (84% yield). Material was then used without further purification. To an 8 mL microwave reaction tube was added 230 µmol acrylamide (70 mg) and 4 mL trifluoroacetic acid. The reaction was run under microwave conditions at 70° C. and 200 W power for 30 minutes. Vessel was removed from microwave reactor and allowed to cool to room temperature. The crude reaction mixture was then transferred to a 50 mL round bottom flask and placed in an ice bath. To it was added 2 mL methylene chloride ($CH_2Cl_2$) and 15 mL saturated sodium bicarbonate with stirring (portion wise, 3×5 mL), followed by extraction with EtOAc (2×10 mL). Organic layers were separated and combined then dried over sodium sulfate. The EtOAc was separated by filtration and concentrated under reduced pressure using a rotary evaporator onto silica gel. The crude material was then purified via flash column chromatography over silica gel with 6:4 hexanes:EtOAc as the eluent to yield 8-(2-ethoxyphenyl)-7,8-dihydro-[1,3]dioxolo[4,5-g]quinolin-6(5H)-one (60 mg, 193 µmol). $^1$H NMR (400 MHz, CHLOROFORM-d) δ ppm 1.34 (t, J=7.03 Hz, 3 H), 2.72-2.92 (m, 2 H), 3.95-4.04 (m, 2 H), 4.53 (t, J=6.64 Hz, 1 H), 5.84 (s, 2 H), 6.32 (s, 1 H), 6.40 (s, 1 H), 6.73-6.78 (m, 2 H), 6.81 (d, J=8.60 Hz, 1 H), 7.13 (m, 1 H), 8.03 (br. s., 1 H). $^{13}$C NMR (126 MHz, CHLOROFORM-d) δ ppm 14.88 (s) 35.69 (s) 36.72 (s) 63.51 (s) 97.80 (s) 101.15 (s) 111.40 (s) 118.68 (s) 120.57 (s) 128.19 (s) 128.29 (s) 129.74 (s) 131.80 (s) 143.57 (s) 146.98 (s) 156.16 (s) 171.72 (s) FTIR $CM^{-1}$ 3208, 2982, 2895, 1677, 1482, 1233, 1039. Low Res MS: Calculated Formula Weight ($C_{18}H_{17}NO_4$)=311.3. Observed M+1 ion=312.

Example 2

Synthesis of 5-(2-ethoxyphenyl)-4,5-dihydro-[1,3]dioxolo[4,5-g][1,2,4]triazolo[1,5-a]quinoline (Compound VII—Racemic mixture of compounds IV and V)

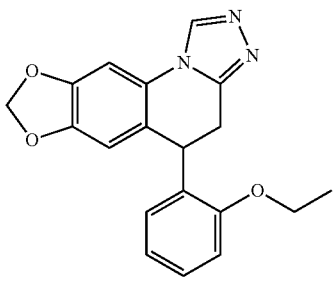

(Structural Formula VII)

FQI-1 (200 mg, 1.0 equiv) was dissolved in 0.96 mL dry acetonitrile and 0.64 mL triethylamine under an atmosphere of nitrogen. Phosphorus pentasulfide (214 mg, 1.5 equiv) was added in one portion and the reaction was heated to 100° C. for 5 hours. The solvent was removed in vacuo and the residue was partitioned between 20 mL methylene chloride and 10 mL brine. The layers were separated and the organic portion was washed with two additional portions of brine, dried over sodium sulfate, and reduced in vacuo. The resultant crude orange foam was dissolved in 1.3 mL n-butanol in a vial under an atmosphere of nitrogen. Acetic acid (8 uL) and formohydrazide (39 mg, 1.0 equiv) were added and the vial was tightly capped and heated to 130° C. for 24 hours. The solvent was removed in vacuo and the residue was suspended in methylene chloride and washed with three portions of brine. The organic layer was dried over sodium sulfate and condensed to give a crude oil that was purified by flash column chromatography (2% to 5% methanol in chloroform). Fractions containing product were pooled to give a brown oil that was recrystallized from chloroform/hexanes to give triazole VIII as a tan solid (40 mg, 19%). $^1$H NMR (500 MHz, CDCl$_3$) δ=8.55 (s, 1 H), 7.21 (ddd, J=1.8, 7.4, 8.2 Hz, 1 H), 6.97 (s, 1 H), 6.89 (dd, J=0.9, 8.2 Hz, 1 H), 6.78 (dt, J=0.9, 7.6 Hz, 1 H), 6.67 (dd, J=1.4, 7.6 Hz, 1 H), 6.60 (d, J=0.6 Hz, 1 H), 6.04-6.00 (m, 2 H), 4.71 (t, J=6.7 Hz, 1 H), 4.08 (dddd, J=2.1, 7.0, 9.3, 16.3 Hz, 2 H), 3.55 (dd, J=7.2, 16.0 Hz, 1 H), 3.35 (dd, J=6.4, 15.9 Hz, 1 H), 1.40 (t, J=7.0 Hz, 3 H). ESI-MS (M+H$^+$) m/z=336.

Example 3

Synthesis of 5-(2-methoxyphenyl)-4,5-dihydro-[1,3] dioxolo[4,5-g][1,2,4]triazolo[1,5-a]quinoline (Compound VIII—Racemic mixture)

(Structural Formula VIII)

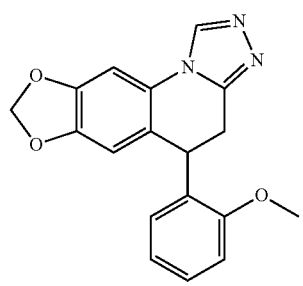

8-(2-methoxyphenyl)-7,8-dihydro-[1,3]dioxolo[4,5-g] quinolin-6(5H)-one (172 mg, 1.0 equiv—prepared essentially as described in Example 1 using 2-methoxycinnamic acid as the starting material) was dissolved in 0.87 mL dry acetonitrile and 0.58 mL triethylamine under an atmosphere of nitrogen. Phosphorus pentasulfide (193 mg, 1.5 equiv) was added in one portion and the reaction was heated to 100° C. for six hours. The solvent was removed in vacuo and the residue was partitioned between 20 mL dichloromethane (DCM) and 10 mL brine. The layers were separated and the organic portion was washed with two additional portions of brine, dried over sodium sulfate, and reduced in vacuo. The resultant crude orange foam was dissolved in 1.1 mL n-butanol in a vial under an atmosphere of nitrogen. Acetic acid (7 uL) and formohydrazide (35 mg, 1.0 equiv) were added and the vial was tightly capped and heated to 130° C. for 24 hours. The solvent was removed in vacuo and the residue was suspended in DCM and washed with three portions of brine. The organic layer was dried over sodium sulfate and condensed to give a crude oil that was purified by flash column chromatography (2% to 5% methanol in chloroform). Fractions containing product were pooled to give a brown oil that was recrystallized from chloroform/hexanes to give triazole compound VIII as a tan solid (50 mg, 27%) that was >99% pure by UPLC-MS (ELSD). $^1$H NMR (400 MHz, CDCl$_3$) δ=8.54 (s, 1 H), 7.21 (ddd, J=1.6, 7.4, 7.8 Hz, 1 H), 6.96 (s, 1 H), 6.89 (d, J=8.2 Hz, 1 H), 6.77 (t, J=7.4 Hz, 1 H), 6.64 (dd, J=1.4, 7.4 Hz, 1 H), 6.56-6.54 (m, 1 H), 5.99 (s, 2 H), 4.67 (t, J=6.6 Hz, 1 H), 3.83 (s, 3 H), 3.50 (dd, J=7.0, 16.0 Hz, 1 H), 3.32 (dd, J=6.3, 16.0 Hz, 1 H). ESI-MS (M+H$^+$) m/z=322.

Example 4

Synthesis of 5-(2-propoxyphenyl)-4,5-dihydro-[1,3] dioxolo[4,5-g][1,2,4]triazolo[1,5-a]quinoline (Compound IX—Racemic mixture)

(Structural Formula IX)

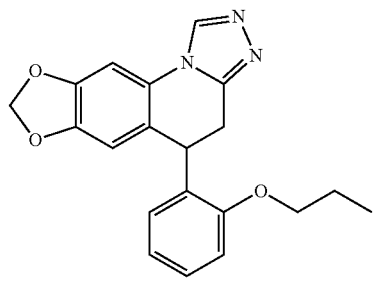

8-(2-propoxyphenyl)-7,8-dihydro-[1,3]dioxolo[4,5-g] quinolin-6(5H)-one (175 mg, 1.0 equiv—prepared essentially as described in Example 1 using 2-propoxycinnamic acid as the starting material) was dissolved in 0.8 mL dry acetonitrile and 0.54 mL triethylamine under an atmosphere of nitrogen. Phosphorus pentasulfide (179 mg, 1.5 equiv) was added in one portion and the reaction was heated to 100° C. for six hours. The solvent was removed in vacuo and the residue was partitioned between 20 mL DCM and 10 mL brine. The layers were separated and the organic portion was washed with two additional portions of brine, dried over sodium sulfate, and reduced in vacuo. The resultant crude orange foam was dissolved in 1.0 mL n-butanol in a vial under an atmosphere of nitrogen. Acetic acid (6 uL) and formohydrazide (31 mg, 1.0 equiv) were added and the vial was tightly capped and heated to 130° C. for 24 hours. The solvent was removed in vacuo and the residue was suspended in DCM and washed with three portions of brine. The organic layer was dried over sodium sulfate and condensed to give a crude oil that was purified by flash column chromatography (2% to 5% methanol in chloroform). Fractions containing product were pooled to give 125 mg of a brown oil that was recrystallized from chloroform/hexanes to give triazole compound IX as a yellow solid (31 mg, 17%) that was >99% pure by UPLC-MS (ELSD). $^1$H NMR (400 MHz, CDCl$_3$) δ=8.54 (s, 1 H), 7.19 (dt, J=2.0, 8.2 Hz, 1 H), 6.99-6.92 (m, 1 H), 6.88 (d, J=8.2 Hz, 1 H), 6.76 (t, J=7.4 Hz, 1 H), 6.65 (dd, J=1.6, 7.8 Hz, 1 H), 6.59-6.54 (m, 1 H), 6.03-5.96 (m, 2 H), 4.67 (dd, J=6.4, 7.4 Hz, 1 H), 4.03-3.88 (m, 2 H), 3.55 (dd, J=7.4, 16.2 Hz, 1 H), 3.33 (dd, J=6.4, 16.2 Hz, 1 H), 1.78 (qd, J=7.1, 13.9 Hz, 2 H), 0.98 (t, J=7.4 Hz, 3 H). ESI-MS (M+H$^+$) m/z=350.

Example 5

Synthesis of 5-(2-ethoxyphenyl)-[1,3]dioxolo[4,5-g][1,2,4]triazolo[1,5-a]quinoline (VI)

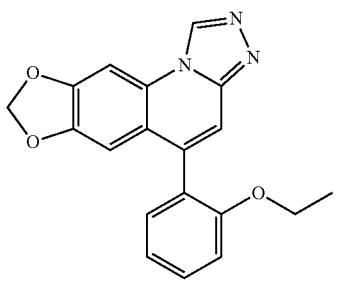

(Structural Formula VI)

8-(2-ethoxyphenyl)-[1,3]dioxolo[4,5-g]quinolin-6(5H)-one—Compound VII (200 mg, 1.0 equiv) was weighed into a reaction vial under an atmosphere of nitrogen. POCl$_3$ (2 mL) was added and the reaction was heated to 120° C. for two hours. The reaction mixture was poured over 20 mL ice water and extracted three times with 25 mL ethyl acetate. The combined organics were washed with water and saturated sodium bicarbonate, dried over magnesium sulfate, and condensed in vacuo to give 220 mg of a crude brown solid. Half of this solid was reserved and the other half (110 mg, 1.0 equiv) was dissolved in 1 mL n-butanol in a reaction vial under an atmosphere of nitrogen. Formohydrazide (23 mg, 1.2 equiv) was added in one portion and the vial was tightly capped and heated to 130° C. for 48 hours. The solvent was removed in vacuo and the residue was partitioned between DCM and brine. The organic layer was washed twice with brine, dried over sodium sulfate, and condensed to give a brown residue that was purified by flash column chromatography (3% to 5% methanol in chloroform) Triazole compound VI was isolated as an orange foam (22 mg, 20%) that was >98% pure by UPLC-MS (ELSD). $^1$H NMR (400 MHz, CDCl$_3$) δ=9.13 (s, 1 H), 7.51 (s, 1 H), 7.47 (ddd, J=1.6, 7.8, 8.2 Hz, 1 H), 7.43 (s, 1 H), 7.28 (dd, J=1.6, 7.8 Hz, 1 H), 7.10 (t, J=7.8 Hz, 1 H), 7.05 (d, J=8.2 Hz, 1 H), 6.87 (s, 1 H), 6.15-6.09 (m, 2 H), 5.31 (s, 1 H), 4.03 (q, J=7.0 Hz, 2 H), 1.16 (t, J=7.0 Hz, 3 H). ESI-MS (M+H$^+$) m/z=334.

Example 6

Synthesis of 5-(2-propoxyphenyl)[1,3]dioxolo[4,5-g][1,2,4]triazolo[1,5-a]quinoline (Compound XXX)

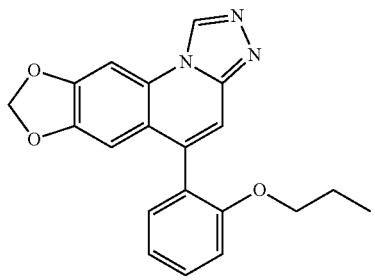

(Structural Formula XXX)

8-(2-propoxyphenyl)[1,3]dioxolo[4,5-g]quinolin-6(5H)-one—Compound IX (180 mg, 1.0 equiv) was weighed into a reaction vial under an atmosphere of nitrogen. POCl$_3$ (2 mL) was added and the reaction was heated to 120° C. for two hours. The reaction mixture was poured over 20 mL ice water and extracted three times with 25 mL ethyl acetate. The combined organics were washed with water and saturated sodium bicarbonate, dried over magnesium sulfate, and condensed in vacuo to give 190 mg of a crude brown solid, which was dissolved in 1.7 mL n-Butanol in a reaction vial under an atmosphere of nitrogen. Formohydrazide (40 mg, 1.2 equiv) was added and the reaction was heated to 130° C. After 48 hours, additional formohydrazide (10 mg, 0.3 equiv) was added and the reaction was heated to 130° C. for an additional 24 hours. The reaction mixture was then condensed in vacuo and partitioned between DCM and brine. The organic layer was washed twice with brine, dried over sodium sulfate, and condensed to give a brown residue that was purified by flash column chromatography (100% chloroform to 2% to 5% methanol in chloroform.) Product was isolated (104 mg) as a brown oil that was contaminated with starting quinioline. The oil was re-purified by a second column (100% diethyl ether followed by a gradient of 1% to 2% to 5% to 10% ethanol in diethyl ether) to give analytically pure triazole compound XXX ((30 mg, 16%, >98% pure by UPLC-MS ELSD). $^1$H NMR (400 MHz, CDCl$_3$) δ=9.13 (s, 1 H), 7.50 (s, 1 H), 7.46 (ddd, J=1.2, 7.4, 8.2 Hz, 1 H), 7.43 (s, 1 H), 7.28 (dd, J=1.2, 7.4 Hz, 1 H), 7.09 (t, J=7.4 Hz, 1 H), 7.04 (d, J=8.2 Hz, 1 H), 6.87 (s, 1 H), 6.11 (d, J=7.0 Hz, 2 H), 3.96-3.84 (m, 2 H), 1.53 (sxt, J=7.0 Hz, 2 H), 0.70 (t, J=7.0 Hz, 3 H). ESI-MS (M+H$^+$) m/z=348.

Example 7

Synthesis of 8-(2-ethoxyphenyl)-7,8-dihydro-[1,3]dioxolo[4,5-g]quinoline-6(5H)-thione (Compound X—Racemic mixture of compounds I and II)

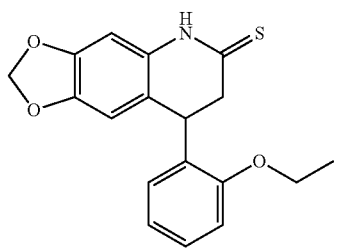

(Structural Formula X)

FQI-1 (200 mg, 1.0 equiv) was weighed into a dry reaction vial under an atmosphere of nitrogen. Dry toluene (4.3 mL) was added, followed by Lawesson's reagent (416 mg, 1.6 equiv). The vial was tightly sealed and the reaction was heated to reflux overnight. After cooling, the solvent was removed in vacuo and the residue was purified by flash column chromatography (gradient of 20% to 70% ethyl acetate in hexanes). Fractions which contained product were pooled to give 120 mg of an impure red oil which was recrystallized from dichloromethane/hexanes to give Compound X as white needles (40 mg, 19%). 1H NMR (400 MHz, CDCl3) δ=9.69 (br. s., 1 H), 7.20 (ddd, J=2.9, 6.0, 8.3 Hz, 1 H), 6.89-6.82 (m, 3 H), 6.46 (d, J=3.1 Hz, 2 H), 5.93 (d, J=1.2 Hz, 2 H), 4.54 (dd, J=6.4, 7.8 Hz, 1 H), 4.10-4.02 (m, 2 H), 3.42 (dd, J=7.8, 17.0

Hz, 1 H), 3.23 (dd, J=6.4, 17.0 Hz, 1 H), 1.40 (t, J=7.0 Hz, 3 H). ESI-MS (M+H+) m/z=328.

Example 7

Synthesis of 8-(2-ethoxyphenyl)[1,3]dioxolo[4,5-g]quinolin-6(5H)-thione (Compound III)

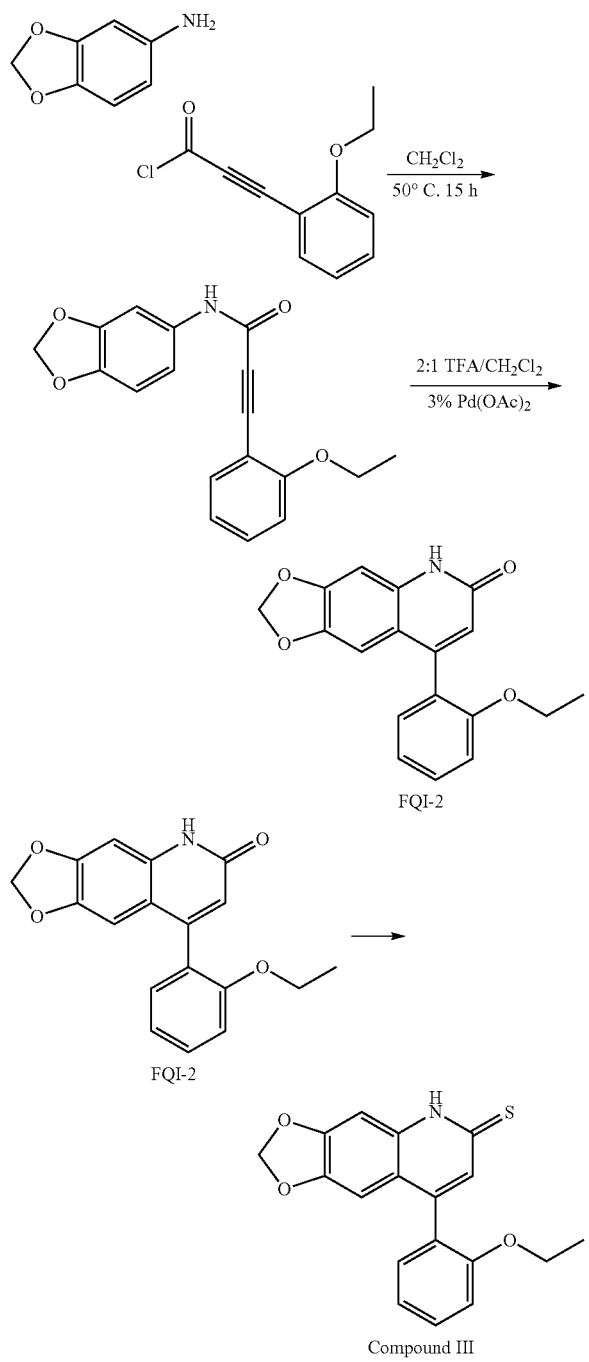

To a flame-dried 250 mL round bottom flask equipped with a stir bar was added 5 mmol (950 mg) 3-(2-ethoxyphenyl)propiolic acid, 100 mL toluene, and 7.5 mmol (1.5 mL) thionyl chloride. The reaction was heated to 85° C. and allowed to stir at this temp for 12 h and then cooled to room temperature. The solvent was removed under reduced pressure and the resulting crude material was then azeotroped (2×25 mL toluene) to remove excess thionyl chloride. The resulting material was dried under high vacuum for 2 hours and made into a 1.0 M solution in $CH_2Cl_2$. To a 25 mL round bottom flask fitted with stir bar and flame dried under vacuum was added 5 mL $CH_2Cl_2$, 1.0 mmol (1 mL, 1.0 M solution in $CH_2Cl_2$) acyl chloride (prepared as described above) and 1.1 mmol (151 mg) benzo[d][1,3]dioxol-5-amine. Reaction was brought to 50° C. and stirred at this temperature for 15 h. Reaction was cooled to room temperature, quenched by addition of 10 mL saturated sodium bicarbonate, extracted with EtOAc (2×10 mL), dried over sodium sulfate, filtered and concentrated in vacuo. Crude material was then dissolved in minimal $CH_2Cl_2$ (5 mL) and poured into 20 mL ice cold hexane. N-(benzo[d][1,3]dioxol-5-yl)-3-(2-ethoxyphenyl)propiolamide precipitated from solution and was isolated via filtration, washed with ice cold diethyl ether (10 mL) and dried under high vacuum for 2 h to yield 309 mg of the desired propargyl amide. The resulting material was used without further purification. To a flame dried 10 mL round bottom flask fitted with stir bar was added 84 mg propargyl amide (0.270 mmol, 1 equiv), 500 uL $CH_2Cl_2$, 1 mL trifluoroacetic acid, and 3 mg Pd(OAc)$_2$(0.01 mmol, 0.05 equiv). Reaction was allowed to stir at room temperature 2 hours and then quenched by addition of 10 mL saturated ammonium chloride, extracted with $CH_2Cl_2$ (3×10 mL), dried over sodium sulfate, $CH_2Cl_2$ isolated via filtration, concentrated onto silica gel and isolated via flash column chromatography over silica gel with 7:3 hexanes:EtOAc as the eluent to yield 8-(2-ethoxyphenyl)-[1,3]dioxolo[4,5-g]quinolin-6(5H)-one. Residual palladium (Pd) was then scavenged by treating with macroporous polystyrene-bound trimercaptotriazine (MP-TMT) resin (15 mg) in 5 mL tetrahydrofuran (THF) for 24 hours at room temperature. Material was then filtered through a pad of celite, and celite washed with $CH_2Cl_2$ (2×10 mL). $CH_2Cl_2$ solution was then concentrated onto silica gel and purified via a second silica gel column with eluent 7:3 hexanes:EtOAc to give purified 8-(2-ethoxyphenyl)-[1,3]dioxolo[4,5-g]quinolin-6(5H)-one-FQI-2 (65 mg, 232 µmol). The material was determined to be >95% pure by $^1$H NMR, $^{13}$C NMR, and HPLC-MS. $^1$H NMR (500 MHz, CHLOROFORM-d) δ ppm 1.12 (t, J=6.97 Hz, 3 H), 3.95 (m, 2 H), 5.91 (d, J=1.22 Hz, 2 H), 6.47 (s, 1 H), 6.55 (s, 1 H), 6.90 (s, 1 H), 6.95 (d, J=8.56 Hz, 1 H), 6.99 (m, 1 H), 7.15 (d, J=7.34 Hz, 1 H), 7.35 (m, 1 H), 12.98 (br. s., 1 H). $^{13}$C NMR (126 MHz, CHLOROFORM-d) δ ppm 14.60 (s), 63.96 (s), 96.33 (s), 101.62 (s), 104.48 (s), 112.29 (s), 114.87 (s), 118.72 (s), 120.69 (s), 126.86 (s), 130.08 (s), 130.48 (s), 135.55 (s), 144.13 (s), 150.43 (s), 150.99 (s), 155.71 (s), 164.40 (s). FTIR $CM^{-1}$ 2978, 2886, 1653, 1487, 1251, 1037. Low Res MS: Calculated Formula Weight ($C_{18}H_{15}NO_4$)=309.3. Observed M+1 ion=310.

To a flame dried reaction tube fitted with stir bar and kept under argon atmosphere was added 117.7 mg FQI-2 (0.37 mmol), 3 mL toluene and 84 mg lawesson's reagent. The solution was brought to 110° C. and allowed to stir 30 minutes. The reaction was then cooled to room temperature and quenched by the addition of 25 mL water, extracted with $CH_2Cl_2$ (2×20 mL), dried over sodium sulfate, filtered through a cotton plug impregnated on silica gel. The recovered material was then purified by column chromatography with eluant 70:30 hexane:EtOAc to give thiocarbonyl product (Compound III).

Example 9

Chiral HPLC Separation of FQI-1 to (R)-FQI-1 and (S)-FQI-1

To a 1.5 mL HPLC vial was added 10 mg of FQI-1 and 1 mL of an 8:1:1 mixture of Hexane:Isopropanol:Chloroform.

Solution was sonicated for 30 minutes to ensure complete dissolution. An Agilent 1100 Series HPLC fitted with analytical ChiralCel OD column (10μ particle size, 4.6 mm ID, 250 mm length) was primed for 30 minutes with a 20% isopropanol in Hexane mixture at a flow rate of 1 mL/min. After priming, 100 μL of the FQI-1 solution was injected onto the column and allowed to separate. Starting from the 9 minute mark, a number of collections were made from the end of the column into a series of 1.5 mL HPLC vials every 15 seconds (24 vials in all with ~250 μL collected in each vial). After the 15 minute mark, the vials were diluted to 750 μL with a 20% isopropanol in hexane mixture and analyzed for enantiopurity. All vials containing material with an er of >95:5 were collected and combined. This procedure was repeated 20 times and produced 7 mg of (S)-FQI-1 (retention time of 9.6 minutes, $[\alpha]_D^{23}=-8.5°$ (c=0.47, CHCl$_3$) er>99:1) and 10 mg of (R)-FQI1 (retention time of 10.6 minutes, $[\alpha]_D^{23}=+10.5$ (c=0.67, CHCl$_3$) er>99:1).

(S)-FQI-1. Retention time 9.6 minutes. (R)-FQI1. Retention time 10.6 minutes.

Optical Rotation and Determination of Absolute Stereochemistry of (S)-FQI-1 and (R)-FQI-1

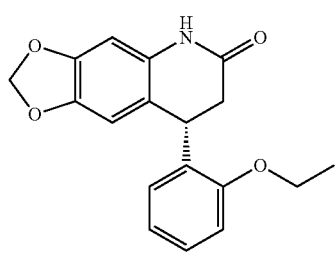

(S)-FQI-1

(-)-(S)-FQI-1 $[\alpha]_D^{23} = -8.5°$
(c = 0.47, CHCl$_3$, er = 99:1)

Compounds known in the literature and used for comparative analysis of optical rotation. (Paquin, J. F., Stephenson, C. R., Defieber, C. & Carreira, E. M. Catalytic asymmetric synthesis with Rh-diene complexes: 1,4-addition of arylboronic acids to unsaturated esters. Org. Lett. 7, 3821-3824 (2005); Chen, G., Tokunaga, N. & Hayashi, T. Rhodium-catalyzed asymmetric 1,4-addition of arylboronic acids to coumarins: asymmetric synthesis of (R)-tolterodine. Org. Lett. 7, 2285-2288 (2005)

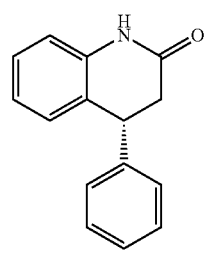

a $[\alpha]_D^{23} = -53.4°$ (R)-FQI-1

-continued

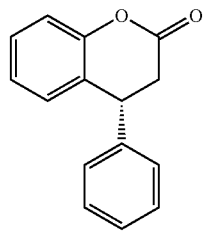

b $[\alpha]_D^{23} = -45.2°$

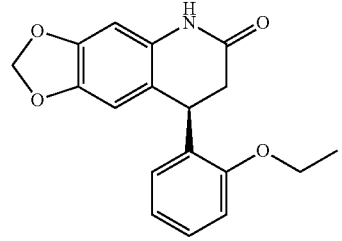

(+)-(R)-FQI-1 $[\alpha]_D^{23} = +10.5$ (c = 0.67, CHCl$_3$, er = 99:1)

Compounds known from the literature and used for comparative analysis of optical rotation. (Defieber, C., Paquin, J. F., Serna, S. & Carreira, E. M. Chiral[2.2.2] dienes as ligands for Rh(I) in conjugate additions of boronic acids to a wide range of acceptors. Org. Lett. 6, 3873-3876 (2004); Alper, H. & Dong, C. Enantioselective cyclocarbonylation of 2-vinylanilines to six-membered lactams. Tetrahedron: Asymmetry 15, 35-40 (2004).)

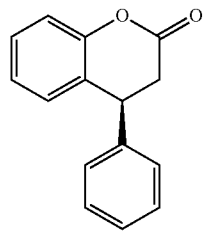

c $[\alpha]_D^{23} = +37.4$

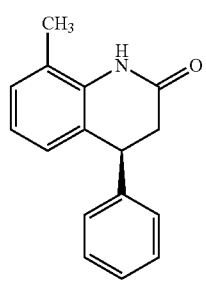

d $[\alpha]_D^{23} = +21.6$

Comments: In this Example 9 the enantiomers of a racemic mixture were separated. In several of the above synthetic procedures, racemic mixtures are produced (e.g. Compounds VII, VIII, IX and X). In each case, the enantiomers of the racemic mixture can be isolated essentially as described above. In particular (but not by way of limitation), the enantiomers of compound VII (i.e. compounds V and VI) can be isolated, the enantiomers of compound X (i.e. compounds I and II) can be isolated.

It should also be appreciated by one of skill in the art that structural formulas provided herein are written according to convention but are meant to exclude alternative equivalent structures that one of skill in the art would appreciate. In particular, the thio-containing compounds (e.g. I, II, and III) can be illustrated in tautomeric forms such as is shown in FIG. 1 (bottom) for compound III.

Example 10

LSF-dependent Reporter Assays

NIH 3T3 cells were transfected with the expression construct pEF1α-LSF, an LSF expression vector[1,2]; the reporter construct pGL3B-WT4E1b, a firefly luciferase reporter vector driven by LSF[3]; phRL-TK, a control renilla luciferase reporter vector; and pEFGP, essentially as previously described[3]. Five hours after transfection, either vehicle (DMSO) or compounds (VI, I and II, IV and V) were added (FIG. 7, FIG. 5 and FIG. 6, respectively), keeping DMSO at 0.5%. Cell extracts were harvested 36 hours post-transfection and firefly and renilla luciferase activities measured via a dual luciferase assay (Promega). Five µl of extract was mixed with 30 µl of luciferase assay reagent (Promega), and luminescence measured for 10 seconds using a 20/20n luminometer (Turner Biosystems). Subsequently, 30 µl of Stop & Glo reagent (Promega) was added, and luminescence also measured for 10 seconds. LSF transactivation activity is given as relative luciferase activity, the ratio of firefly to renilla activities, and normalized to the relative luciferase activity in the presence of vehicle alone. Data for this assay are shown in graphically in FIGS. 5-7.

Example 11

Mouse Xenograft Assays

Figure 8:
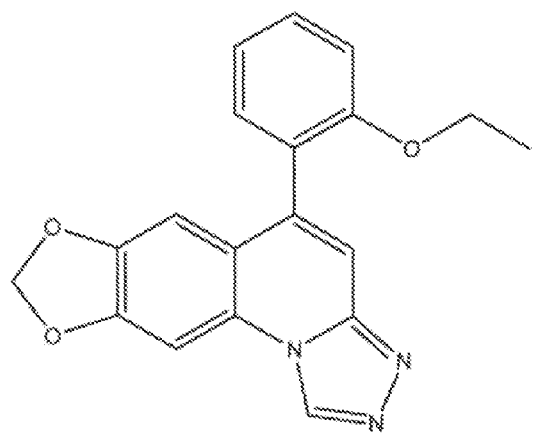
FIG. 8 is: (i) an illustration of the non-chiral triazole-containing therapeutic compound of structural formula VI (also known as LB-242); and (ii) a graphic illustration of data for the treatment of mice with the compound of structural formula VI. In this study nude mice were injected subcutaneously with QGY-7703 cells, and once tumors reached an average size of 200 mm³, they were treated as indicated with either "VI" or vehicle in phosphate buffered saline (PBS).
Figure 8:
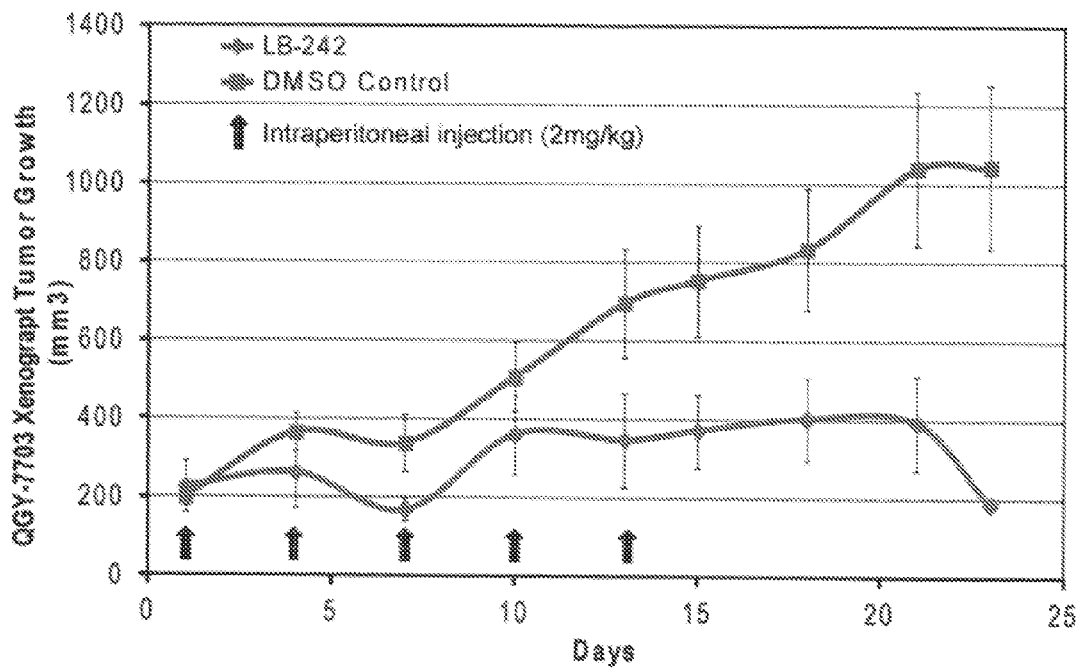

Subcutaneous xenografts were established into the flanks of athymic nude mice using QGY-7703 cells ($5 \times 10^5$) as previously described[4]. When the tumors reached a volume of ~200 $mm^3$ (requiring about a week) intraperitoneal injection of Compound VI (2 mg(VI)/kg of total mouse weight) or vehicle (DMSO control) in phosphate-buffered saline was given 5 times once every 3 days over a period of 2 weeks. The animals were followed for another 2 weeks. Tumor volumes obtained for this experiment is illustrated graphically in FIG. 8.

7. References

[1] Powell, C. M. H., et al. Inhibition of the mammalian transcription factor LSF induces S-phase-dependent apoptosis by downregulating thymidylate synthase expression. EMBO J. 19, 4665-4675 (2000)

[2] Drouin, E. E., Schrader, C. E., Stavnezer, J. & Hansen, U., The ubiquitously expressed DNA-binding protein Late SV40 Factor binds Ig switch regions and represses class switching to IgA. J Immunol 168, 2847-2856 (2002).

[3] Saxena, U. H., et al. Phosphorylation by cyclin C/cyclin-dependent kinase 2 following mitogenic stimulation of murine fibroblasts inhibits transcriptional activity of LSF during G1 progression. Mol Cell Biol. 29, 2335-2345 (2009).

[4] Yoo, B. K., et al. Transcription factor Late SV40 Factor (LSF) functions as an oncogene in hepatocellular carcinoma. Proc. Natl. Acad. Sci. USA 107, 8357-8362 (2010).

[5] El-Serag H B, Rudolph K L Hepatocellular carcinoma: Epidemiology and molecular carcinogenesis. Gastroenterology 132:2557-2576 (2007).

[6] Jemal A, et al. (2008) Cancer statistics, 2008. CA Cancer J Clin 58:71-96.

[7] Parkin D M, Bray F, Ferlay J, Pisani P, Global cancer statistics, 2002. CA Cancer J Clin 55:74-108 (2005).

[8] Huang J H, Liao W S, Synergistic induction of mouse serum amyloid A3 promoter by the inflammatory mediators IL-1 and IL-6. J Interferon Cytokine Res 19:1403-1411 (1999).

[9] Bing Z, Huang J H, Liao W S, NFkappa B interacts with serum amyloid A3 enhancer factor to synergistically activate mouse serum amyloid A3 gene transcription. J Biol Chem 275:31616-31623 (2000).

[10] Llovet J M, Brú C, Bruix J, Prognosis of hepatocellular carcinoma: The BCLC staging classification. Semin Liver Dis 19:329-338 (1999).

[11] Porta-de-la-Riva M, et al., J. Biochem. 435:563-8 (2011)

[12] Bruni, P., G. Minopoli, T. Brancaccio, M. Napolitano, R. Faraonio, N. Zambrano, U. Hansen, and T. Russo, Fe65, a ligand of the Alzheimer's b-amyloid precursor protein, blocks cell cycle progression by down-regulating thymidylate synthase expression. J Biol Chem 277:35481-35488 (2002)

[13] Hansen, U., L. Owens, and U. H. Saxena, Transcription factors LSF and E2Fs: Tandem cyclists driving G0 to S? Cell Cycle 8:2146-2151 (2009)

[14] Swendeman, S. L., C. Spielholz, N. A. Jenkins, D. J. Gilbert, N. G. Copeland, and M. Sheffery, Characterization of the genomic structure, chromosomal location, promoter, and developmental expression of the a-globin transcription factor CP2. J Biol Chem 269:11663-11671 (1994)

[15] Traylor-Knowles, N., U. Hansen, T. Q. Dubuc, M. Q. Martindale, L. Kaufman, and J. R. Finnerty, The evolutionary diversification of LSF and Grainyhead transcription factors preceded the radiation of basal animal lineages. BMC Evolutionary Biology 10:101 (2010)

[16] Yoo, B. K., L. Emdad, Z. Z. Su, A. Villanueva, D. Y. Chiang, N. D. Mukhopadhyay, A. S. Mills, S. Waxman, R. A. Fisher, J. M. Llovet, P. B. Fisher, and D. Sarkar, Astrocyte elevated gene-1 regulates hepatocellular carcinoma development and progression. J Clin. Invest. 119:465-477 (2009)

While the present teachings are described in conjunction with various embodiments, it is not intended that the present teachings be limited to such embodiments. On the contrary, the present teachings encompass various alternatives, modifications and equivalents, as will be appreciated by those of skill in the art.

It should be understood that the order of steps or order for performing certain actions in the following claims is immaterial so long as the present teachings remain operable or unless otherwise specified. Moreover, in some embodiments, two or more steps or actions can be conducted simultaneously so long as the present teachings remain operable or unless otherwise specified.

We claim:

1. A compound of structural formula XIV, XV or XVI;

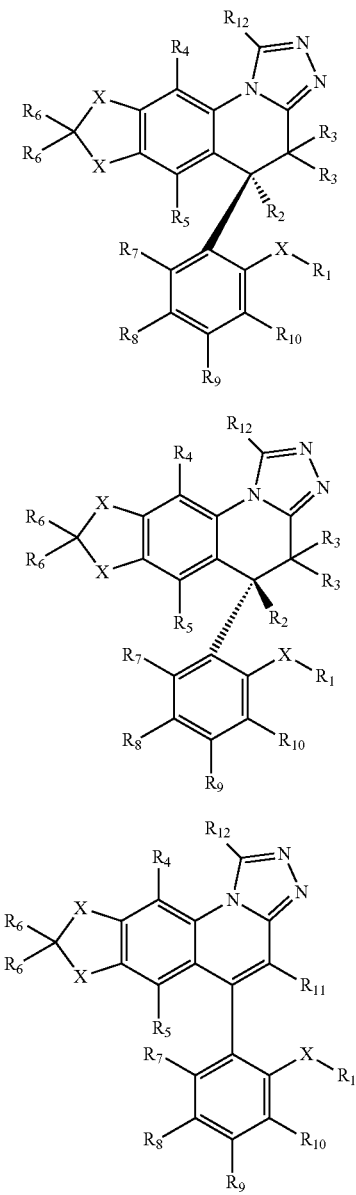

or a pharmaceutically acceptable salt thereof wherein, each X is independently O or S;

$R_1$ is hydrogen or an alkyl, alkenyl, alkynyl, aryl, heteroaryl or arylalkyl group;

$R_2$ is hydrogen or a hydroxyl, alkoxy, phenoxy, alkyl, alkenyl, alkynyl, aryl, heteroaryl or arylalkyl group;

each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

2. The compound of claim 1, wherein for structural formulas XIV, XV or XVI:

each X is O or S;

$R_1$ is hydrogen or a methyl, ethyl, n-propyl, isopropyl, n-butyl, iso-butyl, sec-butyl, substituted or unsubstituted phenyl or substituted or unsubstituted benzyl group;

$R_2$ is hydrogen or a hydroxyl, methoxy, ethoxy, methyl, ethyl, n-propyl, isopropyl, n-butyl, iso-butyl, sec-butyl, phenyl or benzyl group;

each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group.

3. The compound of claim 2, wherein the compound of structural formula XIV, XV or XVI is a compound having the structural formula IV, V or VI;

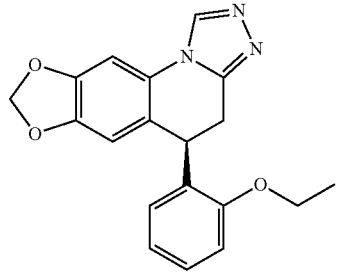

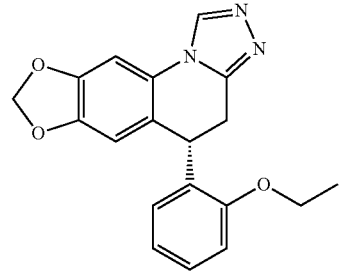

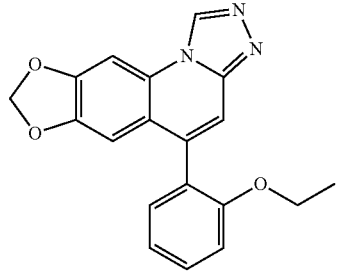

or a pharmaceutically acceptable salt thereof.

4. A composition comprising a compound of formula XIV, XV or XVI;

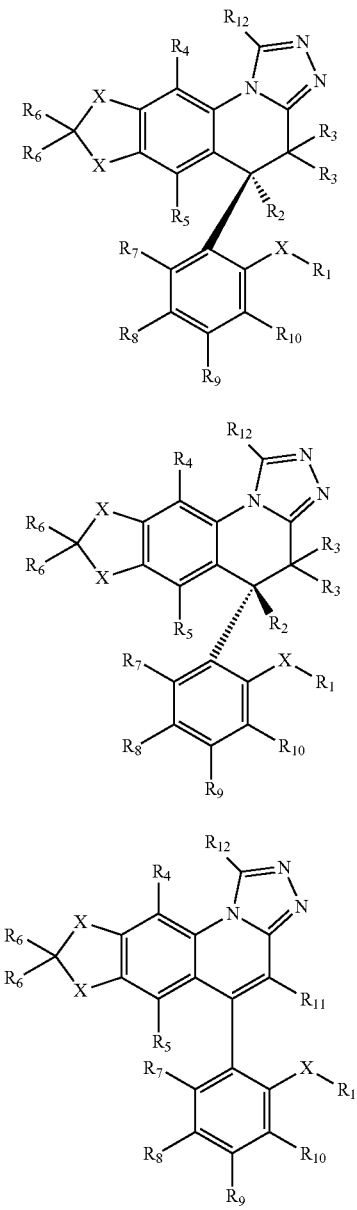

or a pharmaceutically acceptable salt thereof wherein, each X is independently O or S;

$R_1$ is hydrogen or an alkyl, alkenyl, alkynyl, aryl, heteroaryl or arylalkyl group;

$R_2$ is hydrogen or a hydroxyl, alkoxy, phenoxy, alkyl, alkenyl, alkynyl, aryl, heteroaryl or arylalkyl group;

each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and $R_4, R_5, R_7, R_8, R_9, R_{10} R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

5. The composition of claim 4, wherein for the compound of formula XIV, XV or XVI:

each X is O or S;

$R_1$ is hydrogen or a methyl, ethyl, n-propyl, isopropyl, n-butyl, iso-butyl, sec-butyl, substituted or unsubstituted phenyl or substituted or unsubstituted benzyl group;

$R_2$ is hydrogen or a hydroxyl, methoxy, ethoxy, methyl, ethyl, n-propyl, isopropyl, n-butyl, iso-butyl, sec-butyl, phenyl or benzyl group;

each $R_3$ and each $R_6$ is independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group; and $R_4, R_5, R_7, R_8, R_9, R_{10} R_{11}$ and $R_{12}$ are each independently hydrogen, fluorine, chlorine, bromine, iodine or a hydroxyl, methoxy, ethoxy, methyl, ethyl, n-propyl, isopropyl, n-butyl, iso-butyl, sec-butyl, phenyl or benzyl group.

6. The composition of claim 5, wherein the compound of structural formula XIV, XV or XVI is a compound having the structural formula IV, V or VI:

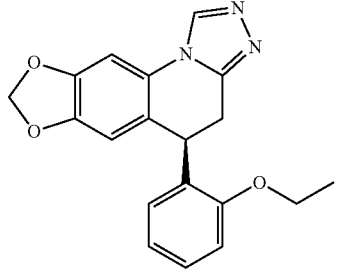

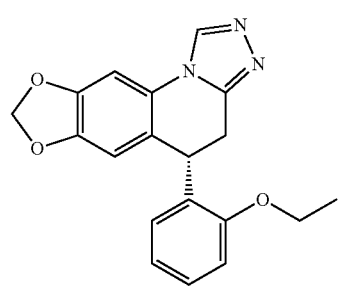

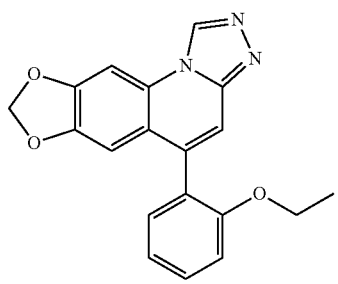

or a pharmaceutically acceptable salt thereof.

7. The composition of claim 4, wherein said composition further comprises a pharmaceutically acceptable carrier.

8. A method comprising administering to a subject, to inhibit or treat LSF in said subject, an effective amount of a compound of structural formula XIV, XV or XVI;

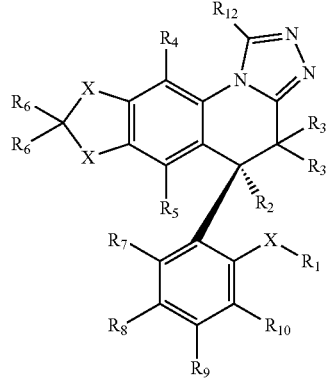

XIV

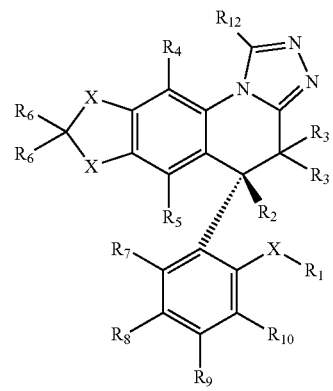

XV

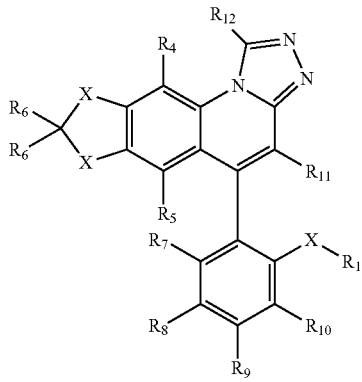

XVI or a pharmaceutically acceptable salt thereof, wherein,
each X is independently O or S;
$R_1$ is hydrogen or an alkyl, alkenyl, alkynyl, aryl, heteroaryl or arylalkyl group;
$R_2$ is hydrogen or a hydroxyl, alkoxy, phenoxy, alkyl, alkenyl, alkynyl, aryl, heteroaryl or arylalkyl group;
each $R_3$ and each $R_6$ is: (i) independently hydrogen, fluorine, chlorine, bromine, iodine or a hydroxyl, alkoxy, phenoxy, alkyl, alkenyl, alkynyl, aryl, heteroaryl or arylalkyl group; or (ii) the two $R_6$ moieties and/or the two $R_3$ moieties taken together with an alkylene, alkenylene or alkynylene group form a substituted or unsubstituted C3 to C6 ring; and
$R_4$, $R_5$, $R_7$, $R_8$, $R_9$, $R_{10}$ $R_{11}$ and $R_{12}$ are each independently hydrogen, fluorine, chlorine, bromine, iodine or a hydroxyl, alkoxy, phenoxy, alkyl, alkenyl, alkynyl, aryl, heteroaryl or arylalkyl group.

9. A method of determining the expression or activity of LSF comprising:
a) contacting a cancerous cell or cancerous tissue with a compound of claim 1; and
b) monitoring, directly or indirectly, the expression or activity of LSF associated with said cancerous cell or cancerous tissue.

10. A method of determining the expression or activity of LSF comprising:
a) contacting a cancerous cell or cancerous tissue with a composition of claim 4; and
b) monitoring, directly or indirectly, the expression or activity of LSF associated with said cancerous cell or cancerous tissue.

* * * * *